(12) United States Patent
Ottonello et al.

(10) Patent No.: US 9,809,866 B2
(45) Date of Patent: Nov. 7, 2017

(54) LIGNOCELLULOSIC BIOMASS HYDROLYSIS WITHOUT ENZYMES OR ACID CATALYSTS

(71) Applicant: Beta Renewables S.p.A., Tortona (IT)

(72) Inventors: Piero Ottonello, Milan (IT); Paolo Torre, Arenzano (IT); Beatriz Rivas Torres, Arenzano (IT); Stefano Paravisi, Tortona (IT); Chiara Prefumo, Genoa (IT); Pietro Pastorino, Campo Ligure (IT)

(73) Assignee: Beta Renewable,m S.p.A., Tortona (AL) (IT)

( * ) Notice: Subject to any disclaimer, the term of this patent is extended or adjusted under 35 U.S.C. 154(b) by 0 days.

(21) Appl. No.: 15/032,640

(22) PCT Filed: Oct. 31, 2014

(86) PCT No.: PCT/EP2014/002927
§ 371 (c)(1),
(2) Date: Apr. 28, 2016

(87) PCT Pub. No.: WO2015/062736
PCT Pub. Date: May 7, 2015

(65) Prior Publication Data
US 2016/0312318 A1    Oct. 27, 2016

(30) Foreign Application Priority Data
Oct. 31, 2013   (IT) .............................. TO2013A0882

(51) Int. Cl.
*C13K 1/02*   (2006.01)
*C13K 13/00*   (2006.01)
(Continued)

(52) U.S. Cl.
CPC ................. *C13K 1/02* (2013.01); *C08H 8/00* (2013.01); *C12P 19/02* (2013.01); *C12P 19/14* (2013.01);
(Continued)

(58) Field of Classification Search
CPC ....................................................... C13K 1/02
See application file for complete search history.

(56) References Cited

U.S. PATENT DOCUMENTS

| | | |
|---|---|---|
| 2009/0056889 A1 | 3/2009 | Ren et al. |
| 2011/0081689 A1 | 4/2011 | Flanegan et al. |

(Continued)

FOREIGN PATENT DOCUMENTS

| | | | |
|---|---|---|---|
| EP | 2610346 A1 | 7/2013 | |
| IT | WO 2013026849 A1 * | 2/2013 | ............... C13K 1/02 |

(Continued)

OTHER PUBLICATIONS

Xiaowen Chen, "Comparison of different mechanical refining technologies on the enzymatic digestibility of low severity acid pretreated corn stover", Bioresource Technology, Jul. 29, 2013, pp. 401 to 408, vol. 147.

(Continued)

*Primary Examiner* — Melvin C Mayes
*Assistant Examiner* — Stefanie Cohen
(74) *Attorney, Agent, or Firm* — Edwin A. Sisson, Attorney at Law, LLC; Jeffrey J. Banyas

(57) ABSTRACT

This specification describes a process of producing a monomeric sugar stream ligno-cellulosic biomass without enzymes or acid catalysts. This is accomplished by removing the water soluble C5 sugars from the ligno-cellulosic biomass feedstream, lowering the pH of the C5 solution with little or no addition of an acid, thermally treating the remaining ligno-cellulosic biomass, combining the thermally treated ligno-cellulosic biomass with the low pH C5 solution and then exposing the mixture to an elevated temperature greater than 80° C. for a time sufficient to hydrolyze at least some of the components of the ligno-cellulosic biomass. Preferably, the thermally treated ligno-
(Continued)

Xylans reaction products cellulosic biomass is subjected to a fiber shives reduction step to reduce the amount of long fiber shives.

26 Claims, 20 Drawing Sheets

(51) Int. Cl.
  *D21C 1/02* (2006.01)
  *C08H 8/00* (2010.01)
  *C12P 19/02* (2006.01)
  *C12P 19/14* (2006.01)

(52) U.S. Cl.
  CPC ............ *C13K 13/00* (2013.01); *C13K 13/002* (2013.01); *D21C 1/02* (2013.01); *C12P 2201/00* (2013.01); *Y02E 50/16* (2013.01)

(56) References Cited

U.S. PATENT DOCUMENTS

| | | |
|---|---|---|
| 2012/0138246 A1 | 6/2012 | Christensen et al. |
| 2013/0065289 A1* | 3/2013 | Carlson .................... C12P 7/10 435/165 |

FOREIGN PATENT DOCUMENTS

| | | |
|---|---|---|
| WO | 2005/099854 A1 | 10/2005 |
| WO | 2012/042498 A1 | 4/2012 |

OTHER PUBLICATIONS

Boussaid et al., "Sugar Recovery and Fermentability of Hemicellulose Hydrolysates from Steam-Exploded Softwoods Containing Bark", Biotech. Prog., Sep. 14, 2001, pp. 887 to 892, vol. 17, American Chemical Society and American Institute of Chemical Engineers.

Duarte et al., "Comparison of Two Posthydrolysis Processes of Brewery's Spent Grain Autohydrolysis Liquor to Produce a Pentose-Containing Culture Medium", Applied Biochemistry and Biotechnology, 2004, pp. 1041 to 1058, vol. 113-116, Humana Press Inc.

Girio et al., "Hemicelluloses for fuel ethanol: A review", Bioresource Technology, Feb. 18, 2010, pp. 4775 to 4800, vol. 101, Elsevier Ltd.

Carvalheiro et al. "Hemicellulose biorefineries: a review on biomass pretreatments", Journal of Scientific & Industrial Research, Nov. 2008, pp. 849 to 864, vol. 67.

Shevchenko et al. "Optimization of monosaccharide recovery by post-hydrolysis of the water-soluble hemicellulose component after steam explosion of softwood chips", Bioresource Technology, 2000, pp. 207 to 2011, vol. 72, Elsevier Science Ltd.

Garrote et al. "Generation of xylose solutions from Eucalyptus globulus wood by autohydrolysis-posthydrolysis processes: posthydrolysis kinetics", Bioresource Technology, 2001, pp. 155 to 164, vol. 79, Elsevier Science Ltd.

Garrote et al. "Manufacture of Xylose-Based Fermentation Media from Corncobs by Posthydrolysis of Autohydrolysis Liquors", Applied Biochemistry and Biotechnology, 2001, pp. 195 to 207, vol. 95, Humana Press Inc.

Duarte et al. "Dilute Acid Hydrolysis of wheat Straw Oligosaccharides", Appl. Biochem. Biotechnol., Dec. 1, 2008, pp. 116 to 126, vol. 153, Humana Press.

Kim et al. "Plug-Flow Reactor for Continuous Hydrolysis of Glucans and Xylans from Pretreated Corn Fiber", Energy & Fuels, Jul. 12, 2005, pp. 2189 to 2200, vol. 19, American Chemical Society.

Vazquez et al. "Enzymatic Processing of Crude Xylooligomer Solutions Obtained by Autohydrolysis of Eucalyptus Wood", Food Biotechnology, 2002, pp. 91 to 105, vol. 16, No. 2, Marcel Dekkar, Inc.

\* cited by examiner

WELDING ENGINEERS 30 mm SCREW ARRANGEMENT for 315-4350 except as noted, screws have 30.00 mm constant pitch and 29.72mm flight O.D.

| Item # | # Required | Name | Stem - root Dia(mm) - length (mm) |
|---|---|---|---|
| 1 | 1 | Main compounder screw | cyl - 24.36 - 45.01 |
| 2 | 1 | Aux " " | cyl - 24.36 - 45.01 |
| 3 | 2 | Main Feed Screw | tapered - 19.5 to 24.36 - 157.5 |
| 4 | 2 | Aux " " | tapered - 19.5 to 24.36 - 157.5 |
| 5 | 1 | Main Mill Screw | cyl - 24.36 - 157.5 |
| 6 | 1 | Aux Mill Screw | cyl - 24.36 - 157.5 |
| 7 | 2 | Main compounder screw | cyl - 28.60 - 45.01 (no flights) |
| 8 | 2 | Aux " " | cyl - 28.60 - 45.01 (no flights) |
| 9 | 2 | Main Mill Screw | cyl - 24.36 - 112.5 |
| 10 | 2 | Aux Mill Screw | cyl - 24.36 - 112.5 |
| 11 | 1 | Main compounder screw | cyl - 28.19 - 45.01 |
| 12 | 1 | Aux " " | cyl - 28.19 - 45.01 |
| 13 | 2 | Main Mill Screw | cyl - 22.86 - 157.5 (10.01 pitch) |
| 14 | 2 | Aux " " | cyl - 22.86 - 157.5 (10.01 pitch) |
| 15 | 1 | Main Mill Screw | cyl - 22.86 - 89.84 |
| 16 | 1 | Aux " " | cyl - 22.86 - 89.84 |
| 17 | 1 | Main Mill Screw | cyl - 22.86 - 157.5 |
| 18 | 1 | Aux Extruder Screw | cyl - 22.86 - 153.6 |
| 19 | 1 | Main Extruder Screw | cyl - 24.359 - 180.4 |
| 20 | 11 | Main Connection Stud | |
| 21 | 10 | Aux " " | |

| | screw segment item #'s; from feed | screw length (mm) |
|---|---|---|
| main | 1, 3, 5, 7, 3, 9, 11, 9, 13, 13, 7, 15, 17, 19 | 1620.1 |
| aux | 2, 4, 6, 8, 4, 10, 12, 10, 14, 14, 8, 16, 18 | 1436 |

FIGURE 6

Reaction products of all the experiments

| Composition | | Test 1 | | Test 2 | | Test 3 | | Test 4 | | Test 5 | |
|---|---|---|---|---|---|---|---|---|---|---|---|
| | | Before reaction | After reaction | Before reaction | After reaction | Before reaction | After reaction | Before reaction | After reaction | Before reaction | After reaction |
| MC | %(wt.) | 84,70% | 88,06% | 84,70% | 87,59% | 84,70% | 88,39% | 84,70% | 88,32% | 84,70% | 88,16% |
| WS | %(wt.) | 7,42% | 7,22% | 7,47% | 6,99% | 7,28% | 7,62% | 7,05% | 7,71% | 7,41% | 7,95% |
| WIS | %(wt.) | 7,88% | 4,72% | 7,83% | 5,42% | 8,02% | 3,99% | 8,25% | 3,97% | 7,89% | 3,89% |
| xylobiose | %wt. | 0,14% | 0,03% | 0,10% | 0,02% | 0,14% | 0,03% | 0,09% | 0,02% | 0,09% | 0,03% |
| glucose | %wt. | 0,04% | 1,16% | 0,05% | 0,57% | 0,04% | 1,17% | 0,05% | 1,51% | 0,05% | 1,40% |
| xylose | %wt. | 0,26% | 0,22% | 0,25% | 0,15% | 0,22% | 1,26% | 0,24% | 1,03% | 0,24% | 0,82% |
| arabinose | %wt. | 0,22% | 0,05% | 0,24% | 0,05% | 0,21% | 0,22% | 0,23% | 0,19% | 0,23% | 0,18% |
| formic acid | %wt. | 0,15% | 0,84% | 0,17% | 1,33% | 0,19% | 0,36% | 0,22% | 0,41% | 0,22% | 0,47% |
| acetic acid | %wt. | 0,38% | 0,76% | 0,43% | 0,86% | 0,40% | 0,72% | 0,43% | 0,80% | 0,43% | 0,83% |
| levulinic acid | %wt. | 0,03% | 0,60% | 0,02% | 1,25% | 0,02% | 0,14% | 0,02% | 0,23% | 0,02% | 0,28% |
| 5-HMF | %wt. | 0,01% | 0,21% | 0,01% | 0,10% | 0,01% | 0,13% | 0,01% | 0,13% | 0,01% | 0,13% |
| furfural | %wt. | 0,00% | 0,78% | 0,00% | 0,61% | 0,00% | 0,99% | 0,00% | 0,93% | 0,00% | 1,00% |
| glucolygomers | %wt. | 0,36% | 0,01% | 0,36% | 0,00% | 0,36% | 0,09% | 0,35% | 0,00% | 0,35% | 0,03% |
| xylolygomers | %wt. | 2,28% | 0,00% | 2,35% | 0,00% | 2,34% | 0,00% | 2,18% | 0,00% | 2,18% | 0,00% |
| arabinan | %wt. | 0,21% | 0,00% | 0,24% | 0,00% | 0,15% | 0,02% | 0,16% | 0,00% | 0,16% | 0,00% |
| acetyls | %wt. | 0,44% | 0,52% | 0,46% | 0,61% | 0,37% | 0,42% | 0,37% | 0,43% | 0,37% | 0,43% |
| other | %wt. | 2,90% | 2,03% | 2,78% | 1,43% | 2,83% | 2,07% | 2,70% | 2,04% | 3,06% | 2,35% |
| insoluble glucans | %wt. | 3,72% | 0,42% | 3,29% | 0,12% | 3,87% | 1,46% | 3,90% | 1,29% | 3,90% | 1,26% |
| insoluble xylans | %wt. | 0,81% | 0,00% | 1,07% | 0,00% | 0,98% | 0,00% | 0,84% | 0,00% | 0,84% | 0,00% |
| insoluble arabinan | %wt. | 0,09% | 0,00% | 0,13% | 0,00% | 0,00% | 0,00% | 0,00% | 0,00% | 0,00% | 0,00% |
| insoluble acetyls | %wt. | 0,08% | 0,00% | 0,09% | 0,00% | 0,09% | 0,00% | 0,08% | 0,00% | 0,08% | 0,00% |
| other insoluble | %wt. | 3,18% | 4,30% | 3,25% | 5,30% | 3,09% | 2,54% | 3,43% | 2,67% | 3,07% | 2,63% |
| total | %wt. | 100,00% | 100,00% | 100,00% | 100,00% | 100,00% | 100,00% | 100,00% | 100,00% | 100,00% | 100,00% |
| pH | | 1,12 | 1,25 | 0,97 | 1,12 | 1,12 | 1,26 | 0,97 | 1,12 | 0,97 | 1,09 |

FIGURE 18

LIGNOCELLULOSIC BIOMASS HYDROLYSIS WITHOUT ENZYMES OR ACID CATALYSTS

PRIORITIES AND CROSS REFERENCES

This patent application claims the priority from International Application No. PCT/EP2014/002927 filed on 31 Oct. 2014 and Italian Application No. TO2013A000882 filed on 31 Oct. 2013 the teachings of both of which are incorporated herein by reference in their entirety.

BACKGROUND

Acid hydrolysis of ligno-cellulosic biomass and cellulose is known in the art. It is practiced both in homogenous or heterogeneous manners.

Usually processes to obtain a monomeric sugar stream from an oligomeric sugar stream coming from pre-treated lignocellulosic material (e.g. autohydrolysis, hot water washing or steam explosion) seek to limit the monosaccharide transformation into degradation products during post hydrolysis of the oligosaccharides into monomers. (Duarte et al., 2004; Girio et al, 2010).

Post hydrolysis, also known as hydrolysis, options for the xylo-oligo-saccharides (XOs) hydrolysis are acid catalyzed (Boussaid et al., 2001), or enzymatic catalysed processes (Duarte et al., 2004) (Carvalheiro et al, 2008).

The main factors affecting monosaccharide recovery in dilute-acid chemical post hydrolysis are catalyst concentration, reaction time, and temperature. The acid process was applied to hydrolysates obtained from softwoods (Shevchenko et al., 2000), hardwoods (Garrote et al., 2001a) and herbaceous materials (Garrote et al., 2001b). The main catalyst reported is sulphuric acid (Duarte et al., 2009; Shevchenko et al., 2000), although, other catalysts can be employed (such as phosphoric acid, hydrochloric acid, formic acid). Under fully optimized post hydrolysis conditions, sugar recovery can be close 100% (Duarte et al., 2004, 2009; Garrote et al., 2001a,b; Shevchenko et al., 2000), as compared to the standard dilute acid hydrolysis (121° C., 4% $H_2SO_4$ and 60 min) which is generally used for the quantitative acid hydrolysis of oligosaccharides. During the acid hydrolysis of oligosaccharides, degradation reactions lead to the formations of many compounds, particularly, 5-hydroxymethylfurfural (HMF), furfural, formic and levulinic acids, which can inhibit further bioconversion steps, reducing the sugar yields of the process (Duarte et al, 2009).

Additionally, acid catalysts usually involves increasing the concentration of non-sugar compounds up to a value incompatible with the economic and environmental sustainability.

Kim et al (Youngmi Kim, Rick Hendrickson, Nathan Mosier, and Michael R. Ladisch, "Plug-Flow Reactor for Continuous Hydrolysis of Glucans and Xylans from Pretreated Corn Fiber", Energy & Fuels 2005, 19, 2189-2200), describes a heterogeneous system when the aqueous stream is first contacted with the cation exchanger at room temperature where proteins, phenolics, minerals, and other catalyst fouling components are removed. The material is then passed over a packed-bed of the same catalyst at 130° C. to give 88% hydrolysis for a space time of 105 min.

The process in Kim et al is temperature limited because the catalyst degrades at temperatures greater than 130° C. and catalyst fouling also increases with increasing temperature above than 130° C.

Alternatively, the post hydrolysis of oligosaccharides can be catalysed by enzymes. Because the complex hemicellulose structure is still present in the oligosaccharides obtained from the pre-treatment, the action of several enzyme activities is usually required for the complete hydrolysis (e.g., endoxylanase, exoxylanase, β-xylosidase and accessory activities like acetyl xylanesterase, α-glucuronidase, α-arabinofuranosidase, and feruloyl esterase); hence potentially turning the process uneconomical (Vázquez et al., 2002; Duarte et al, 2009). Moreover, toxic/inhibitors compounds potentially present in the hydrolysate can significantly reduce enzyme activity (Carvalheiro et al, 2008). Regardless of all these aspects, the enzymatic post hydrolysis presents the advantage OF minimizing the monosaccharide degradation reactions.

There exists therefore, a need for a homogeneous acidic catalyzed hydrolysis which produces few degradation products.

SUMMARY

It is disclosed a process for the hydrolysis of C5 and C6 sugars present in a ligno-cellulosic biomass feed stream. The process comprises the steps of A. Pretreating the ligno-cellulosic biomass feed stream to create a pretreated solid ligno-cellulosic biomass stream comprising water insoluble C6 sugars and a liquid biomass solution comprising water soluble C5 sugars, B. Creating an acidic stream from the liquid biomass solution by increasing the number of $H^+$ ions in the liquid biomass solution by an amount sufficient so that the pH of the acidic stream is at least 0.5 pH units less than the pH of the liquid biomass solution prior to the addition of the $H^+$ ions, wherein less than 90% of the total amount of $H^+$ ions added to the acidic stream are derived from an acid or acids, C. Combining at least a portion of the acidic stream comprising water soluble C5 sugars with at least a portion of the water insoluble C6 sugars to create a mixture, and D. Hydrolyzing at least one of the C5 and C6 sugars of the mixture by increasing the temperature of the mixture to a hydrolysis temperature greater than 80° C. for a hydrolysis time greater than 0.5 minute.

It is also disclosed that at least a portion of the $H^+$ ions in the acidic stream may be derived from decationization of the liquid biomass solution using an ion exchange agent and the at least a portion of the acidic stream mixed with the at least a portion of pretreated solid ligno-cellulosic biomass stream comprising water insoluble C6 sugars may be separated from the ion exchange agent before mixing with the at least a pretreated solid ligno-cellulosic biomass stream comprising water insoluble C6 sugars.

It is further disclosed that the percentage of the total amount of $H^+$ ions added to the acidic stream derived from an acid or acids may be selected from the group consisting of less than 80%, less than 70%, less than 60%, less than 50%, less than 40%, less than 30%, less than 20%, less than 10%, and substantially 0%.

It is also disclosed that the pH of the acidic stream may be less than 2.5.

It is further disclosed that at least a portion of the $H^+$ ions may be derived from an acid added to either the feed stream or the acidic stream, or both prior to hydrolysis.

It is also disclosed that at least a portion of the H⁺ ions may be derived from an acid or acids added to the acidic stream during the hydrolysis step.

It is further disclosed that a salt may be added to the process and/or the liquid biomass solution.

It is also disclosed that at least a portion of the salt may be added to the feed stream prior to adding the H⁺ ions to create the acidic stream.

It is further disclosed that the hydrolysis temperature range may be in the range of 80 to 250° C.

It is also disclosed that the hydrolysis time may be within the range of 1 minute to 24 hours.

It is further disclosed that the pretreated solid ligno-cellulosic biomass stream comprising insoluble C6 sugars may be thermally treated via steam explosion to create a thermally treated pretreated solid ligno-cellulosic biomass stream comprising insoluble C6 sugars prior to being combined with the at least a portion of the water soluble C5 sugars.

It is also disclosed that the thermally treated pretreated solid ligno-cellulosic biomass stream comprising insoluble C6 sugars may be subjected to a wash process prior to being combined with the at least a portion of the water soluble C5 sugars.

It is further disclosed that the pretreated solid ligno-cellulosic biomass stream comprising insoluble C6 sugars may be thermally treated to create a thermally treated ligno-cellulosic biomass stream prior to being combined with the at least a portion of the water soluble C5 sugars.

It is also disclosed that the thermally treated ligno-cellulosic biomass may be in the physical forms of at least fibres, fines and fiber shives, wherein:
 a. the fibres each have a width of 75 μm or less, and a fibre length greater than or equal to 200 μm,
 b. the fines each have a width of 75 μm or less, and a fine length less than 200 μm,
 c. the fiber shives each have a shive width greater than 75 μm with a first portion of the fiber shives each having a shive length less than 737 μm and a second portion of the fiber shives each having a shive length greater than or equal to 737 μm;
  wherein the process further comprises the step of reducing the fiber shives of the thermally treated ligno-cellulosic biomass, wherein the percent area of fiber shives having a shive length greater than or equal to 737 μm relative to the total area of fiber shives, fibres and fines of the thermally treated ligno-cellulosic biomass after fiber shives reduction is less than the percent area of fiber shives having a shive length greater than or equal to 737 μm relative to the total area of fiber shives, fibres and fines of the thermally treated ligno-cellulosic biomass before fiber shives reduction, wherein the percent area is measured by automated optical analysis.

It is further disclosed that a part of the fiber shives reduction may be done by separating at least a portion of the fiber shives having a shive length greater than or equal to 737 μm from the thermally treated ligno-cellulosic biomass.

It is also disclosed that a part of the fiber shives reduction may be done by converting at least a portion of the fiber shives having a shive length greater than or equal to 737 μm in the thermally treated ligno-cellulosic biomass to fibres or fines.

It is further disclosed that at least a part of the fiber shives reduction may be done by applying a work in a form of mechanical forces to the thermally treated ligno-cellulosic biomass, and all the work done by all the forms of mechanical forces on the thermally treated ligno-cellulosic biomass is less than 500 Wh/Kg per kg of the thermally treated ligno-cellulosic biomass on a dry basis.

It is also disclosed that all the work done by all the forms of mechanical forces on the thermally treated ligno-cellulosic biomass may be less than a value selected from the group consisting of 400 Wh/Kg, 300 Wh/Kg, 200 Wh/Kg, 100 Wh/Kg, per kg of the thermally treated ligno-cellulosic biomass on a dry basis.

It is further disclosed that the thermally treated ligno-cellulosic biomass before fiber shives reduction may be characterized by having a viscosity of a slurry of the thermally treated ligno-cellulosic biomass before fiber shives reduction in water which is greater than the viscosity of a slurry of the thermally treated ligno-cellulosic biomass after fiber shives reduction in water, wherein the viscosities are measured at 25° C., at a shear rate of 10 s⁻¹ and at a dry matter content of 7% by weight of each slurry.

It is also disclosed that the thermally treated ligno-cellulosic biomass after fiber shives reduction may be characterized by having a viscosity of a slurry of the thermally treated ligno-cellulosic biomass after fiber shives reduction in water less than a value selected from the group consisting of 0.1 Pa s, 0.3 Pa s, 0.5 Pa s, 0.7 Pa s, 0.9 Pa s, 1.0 Pa s, 1.5 Pa s, 2.0 Pa s, 2.5 Pa s, 3.0 Pa s, 4 Pa s, 5 Pa s, 7 Pa s, 9 Pa s, 10 Pa s, wherein the viscosity is measured at 25° C., at a shear rate of 10 s⁻¹ and at a dry matter content of 7% by weight of the slurry of the thermally treated ligno-cellulosic biomass after fiber shives reduction in the water.

It is further disclosed that the percent area of the fiber shives having a shive length greater than or equal to 737 μm relative to the total area of fiber shives, fibres and fines of the thermally treated ligno-cellulosic biomass after fiber shives reduction may be less than a value selected from the group consisting of 5%, 10%, 20%, 30%, 40%, 50%, 60% and 70% of the percent area of the fiber shives having a shive length greater than or equal to 737 μm relative to the total area of fiber shives, fibres and fines of the thermally treated ligno-cellulosic biomass before fiber shives reduction.

It is also disclosed that the percent area of the fiber shives having a shive length greater than or equal to 737 μm relative to the total area of fiber shives, fibres and fines of the thermally treated ligno-cellulosic biomass after fiber shives reduction may be less than a value selected from the group consisting of 1%, 0.5%, 0.25%, 0.2% and 0.1%.

It is further disclosed that the thermally treated ligno-cellulosic biomass may have been steam exploded as part of the thermal treatment.

It is also disclosed that the severity factor of the thermal treatment used to create the thermally treated ligno-cellulosic biomass may be less than a value selected from the group consisting of 4.0, 3.75, 3.5, 3.25, 3.0, 2.75 and 2.5.

It is further disclosed that the thermally treated ligno-cellulosic biomass before fiber shives reduction may have a dry matter content of at least 20% by weight of the total content of the thermally treated ligno-cellulosic biomass before fiber shives reduction.

It is also disclosed that the dry matter content of the thermally treated ligno-cellulosic biomass before fiber shives reduction may be the range of at least a value selected from the group consisting of 25%, 30%, 35%, and 40% by weight of the total content of the thermally treated ligno-cellulosic biomass before fiber shives reduction to less than 80% by weight of the total content of the thermally treated ligno-cellulosic biomass after fiber shives reduction.

BRIEF DESCRIPTION OF FIGURES

FIG. 6 is the screw design of the twin screw extruder used in the experiments.

FIG. 18 shows initial mixtures, composition of reaction products, and final pH, according to one embodiment.

DETAILED DESCRIPTION

Figure 1:
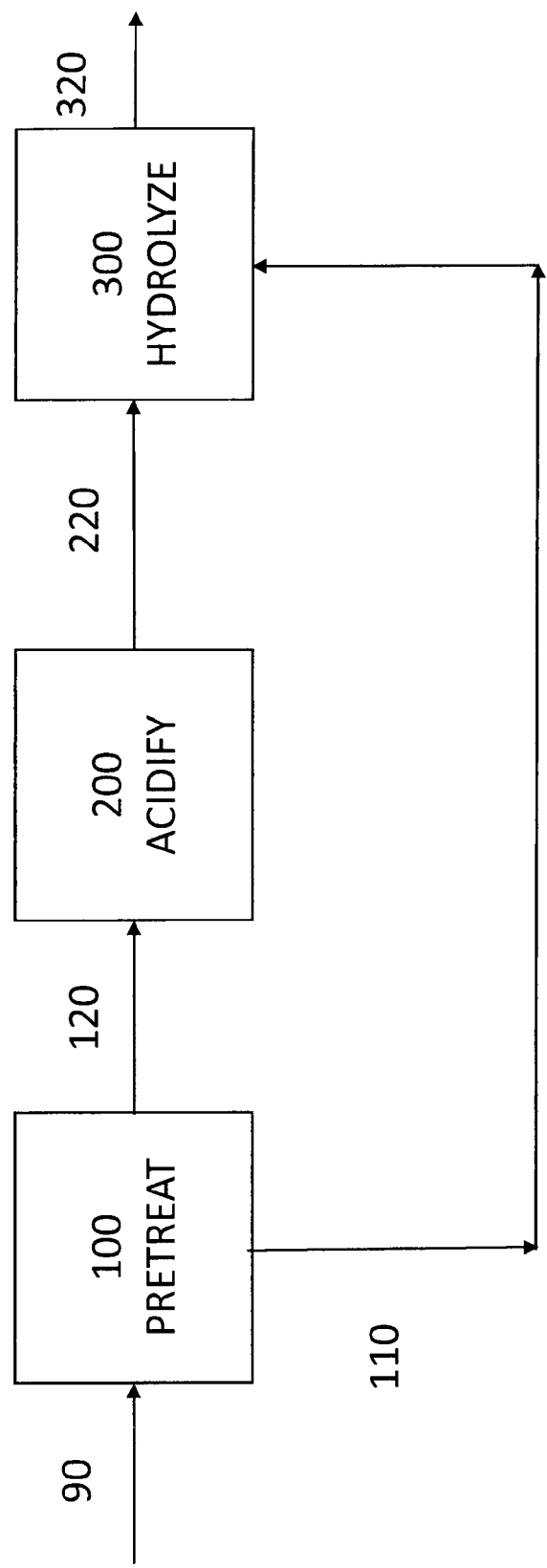
FIG. 1 is a schematic of a first embodiment of the process.

This specification discloses a manner to conduct acidic hydrolysis of a ligno-cellulosic biomass stream by contacting components of the ligno-cellulosic biomass with very little or no conventional acid or acids. Conventional acid(s) are those acids which donate a proton ($H^+$) and will react with a base to form a salt. Conventional acid(s) are not those acids which create an acidic environment by reacting with something else to generate the proton, such as $AlCl_3$ which reacts with water to form HCl, the actual conventional acid. As such, Aluminum Chloride is known as a Lewis Acid and is not considered a conventional acid for the purpose of this specification.

This process is useful for ligno-cellulosic biomass feed streams. This process is also useful for the hydrolysis of pectins, such as those found in fruits like orange peels, apple skins, for example.

It is believed that this process will work on any stream containing polymeric sugars. For example, inulin is the polymer of fructose.

The first step of the process is to pre-treated ligno-cellulosic biomass feedstock, with plant biomass being one such feedstock. Apart from starch, the three major constituents in plant biomass are cellulose, hemicellulose and lignin, which are commonly referred to by the generic term ligno-cellulose. Polysaccharide-containing biomass is a generic term that includes both starch and lignocellulosic biomasses. Therefore, some types of feedstocks can be plant biomass, polysaccharide containing biomass, and lignocellulosic biomass. To be clear, in this specification, a ligno-cellulosic biomass may and/or may not contain starch.

The ligno-cellulosic biomass feedstock will also comprise C5 and C6 sugars. The C5 sugars are arabinan and xylan and the monomers, dimers, oligomers and polymers of arabinose and xylose. The C6 sugars are the glucans which include the monomers, dimers, oligomers and polymers of glucose.

The ligno-cellulosic biomass feedstock can be free of starch, substantially free of starch, or have a starch content of 0. Starch, if present, can be less than 75% by weight of the dry content. There is no preferred starch range as its presence is not believed to affect the hydrolysis of the cellulose. Ranges for the starch amount, if present, are between 0 and 75% by weight of the dry content, 0 to 50% by weight of the dry content, 0 to 30% by weight of the dry content and 0 to 25% by weight of the dry content.

A detailed description of feedstock selection is contained in a following section of the present specification The pre-treatment is used to separate the water soluble C5 sugars into a liquid solution separate from the remaining pre-treated solid ligno-cellulosic biomass. While traditional definitions of pre-treatment include steam explosion, steam explosion is considered a thermal treatment for the purposes of this specification.

In various embodiments, the pre-treatment will be a hydrothermal pre-treatment and chosen using the following soaking conditions: Pre-treatment temperature: 40-250° C., preferably 120-240° C., more preferably 130-230° C., more preferably 140-220° C., more preferably 150-210° C., more preferably 160-200° C., even more preferably 170-200° C. or most preferably 180-200° C.

Regarding the pre-treatment time, there are no particular time requirements, as longer pre-treatment time generally extracts more C5 sugars, but ranges of 1-180 min, 2-55 min, 3-50 min, 4-45 min, 5-40 min, 5-35 min, 5-30 min, 5-25 min, 5-20 min and 5-15 min are suitable.

Such a soaking process is described in WO 2010113129. Preferred thermal treatment are described in a separated section of this specification.

Polysaccharide-containing biomasses according to the present invention include any material containing polymeric sugars e.g. in the form of starch as well as refined starch, cellulose and hemicellulose. However, as discussed earlier, the starch is not necessarily a major component.

As described below, the disclosed process operates upon the principle of the hydrolysis of C5s and C6s of the ligno-cellulosic biomass in the presence of an acidic environment. The hydrolysis of ligno-cellulosic biomass in the presence of an acidic environment is experimentally established in the literature for multiple types of ligno-cellulosic biomass. The unifying concept being the presence of polymeric sugars in the form that can be hydrolyzed in acid environment at elevated temperature. Thus, while the examples are to the disclosed species of ligno-cellulosic biomass, there is no known scientific reason as to why the disclosed process should fail to work upon other ligno-cellulosic biomasses which contain polymeric sugars known to be hydrolyzable in an acidic environment (low pH).

The pre-treated feed streams of ligno-cellulosic biomass usually contain sugars from 20% to 40% of total soluble compounds; while 10% to 20% of non-sugar compounds are inorganic salts. These inorganic salts are often the salts of Calcium and Magnesium cations. While other cations may also be present, the presence of cations is beneficial to the process.

In various embodiments, the liquid biomass feed stream will comprise water, sugars which includes the monomeric sugars and oligomeric sugars, salts which are disassociated into anions and cations in the liquid biomass feed stream, optionally phenols, furfural, oils and acetic acid. The feed stream will in particular contain xyloligomers which are oligomers and polymers contains xylose.

In one embodiment, the concentration of the total sugars in the liquid biomass feed stream should be in the range of 0.1 to 300 g/L, with 50 to 290 g/L being more preferred, and 75 to 280 g/L even more preferred with 100 to 250 most preferred. This implies concentrating the sugars from their natural occurring concentrations after pre-treatment.

The process of this invention comprises the following steps.

The first step is to thermally pre-treat the ligno-cellulosic feedstock with a liquid, usually comprising water to solubilize at least a portion of the water soluble C5 sugars into the liquid. The liquid biomass solution of the water soluble C5 sugars is separated from the insoluble portion of the ligno-cellulosic feed stream, referred to as the pre-treated solid ligno-cellulosic biomass.

At this point there are two streams, one is the pre-treated solid ligno-cellulosic biomass stream. While the pre-treated solid ligno-cellulosic biomass stream will comprise water, there may be some free water or water not absorbed by the insoluble ligno-cellulosic biomass. This stream will also comprise lignin and cellulose and may comprise a portion of the water soluble C5 sugars and a portion of not solubilized C5 sugars.

The liquid used to solubilize the water soluble C5 sugars usually comprises, or is, water. Once separated from the pretreated solid ligno-cellulosic biomass this liquid biomass solution comprising water soluble C5 sugars is used to create the acidic stream. The liquid biomass solution may not be completely free of solids as small particles of insolubles may carry over and be present in the liquid solution as well. The acidic stream is created from the liquid biomass solution by increasing the amount of $H^+$ ions in the liquid biomass solution.

After the desired pH is obtained, the acid stream is combined with the water insoluble C6s in the pretreated solid ligno-cellulosic biomass stream to create a mixture.

At least one of the C5' and C6 sugars are hydrolyzed by raising the temperature of the mixture to a hydrolysis temperature for the hydrolysis reaction to occur creating a hydrolyzed stream.

After hydrolysis, the hydrolyzed stream can be passed to other unit operations for further processing.

What has been discovered from this process is that the hydrolysis can occur when the H+ ions are increased by cationic exchange. In this manner, the pH is lowered but without the presences of the counterion which is often detrimental to the downstream processes after hydrolysis. This method also eliminates or reduces the use of enzymes for hydrolysis. It is almost as if it is acid hydrolysis without an acid.

FIG. 1 is the simplest embodiment of the invention. The ligno-cellulosic biomass feed stream (90) is pretreated in step or vessel (100). The pretreated solid ligno-cellulosic biomass stream comprising water insoluble C6 sugars is removed as stream 110. Liquid biomass solution stream comprising water soluble C5 sugars (120) is then acidified, or has the amount of $H^+$ ions increased at step 200, which in one embodiment, is accomplished by cationic exchange as described in the experimental section and in PCT/EP2012/066263. The acidic stream (220) is combined with the pretreated solid lignocellulosic biomass stream comprising water insoluble C6 sugars, which was removed as stream 110, in the hydrolysis step 300.

The hydrolysis step (300) is performed by increasing the temperature of contents of 300, the mixture, to a hydrolysis temperature above 80° C. for a hydrolysis time. The hydrolysate is then removed as stream 320. Of course, this can be done on a continuous basis as well as a batch operation.

Figure 2:
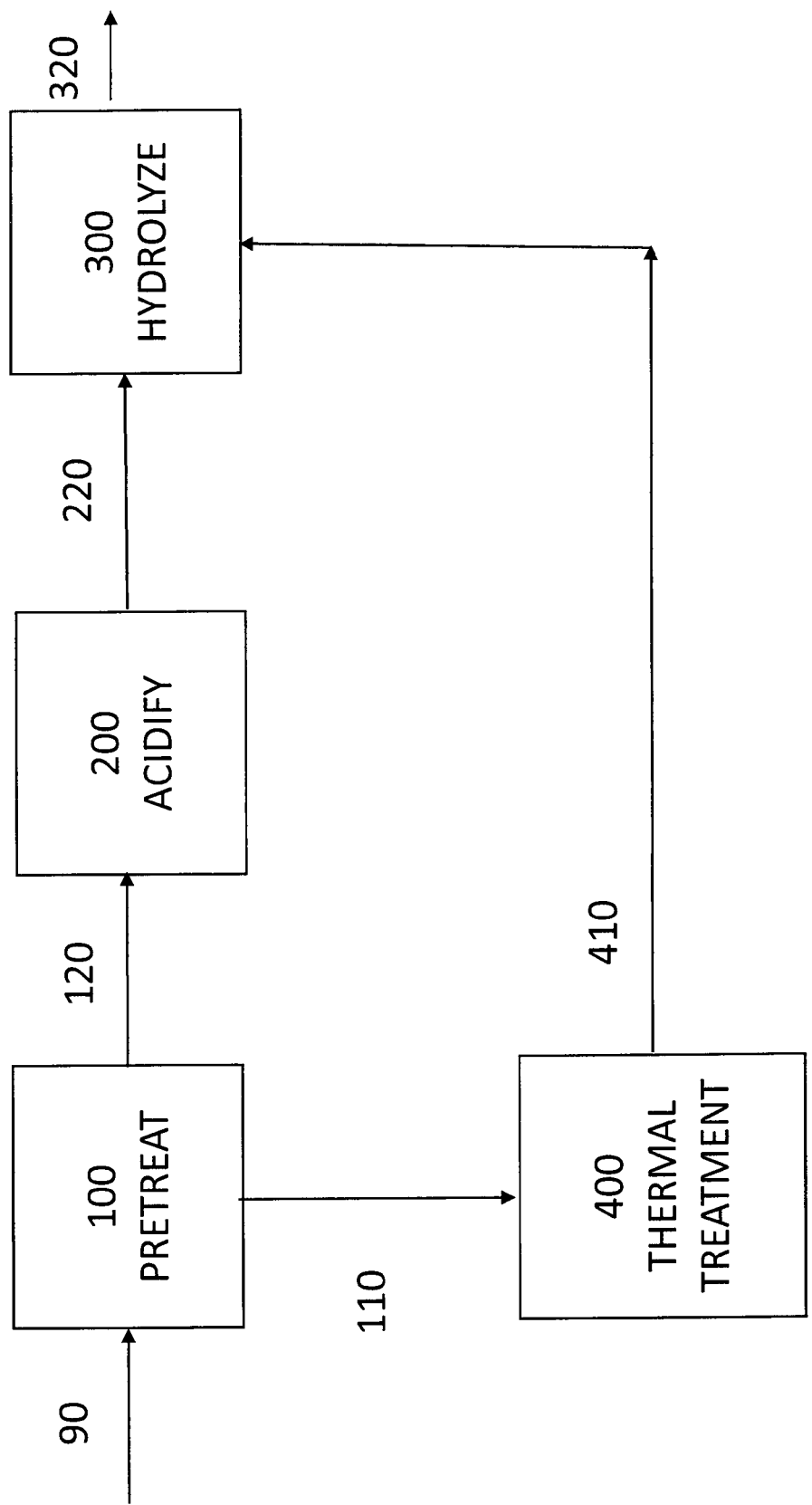
FIG. 2 is a schematic of a second embodiment of the process.

In another embodiment, Embodiment Number 2 (FIG. 2), the process includes step 400, the thermal pretreatment, which in various embodiment is steam explosion. Steam explosion is well known in the art and can also be found in WO2010113129. The thermally pretreated stream (410) is passed on to the hydrolysis process where it is combined with the acidic stream (220) for hydrolysis.

Figure 3:
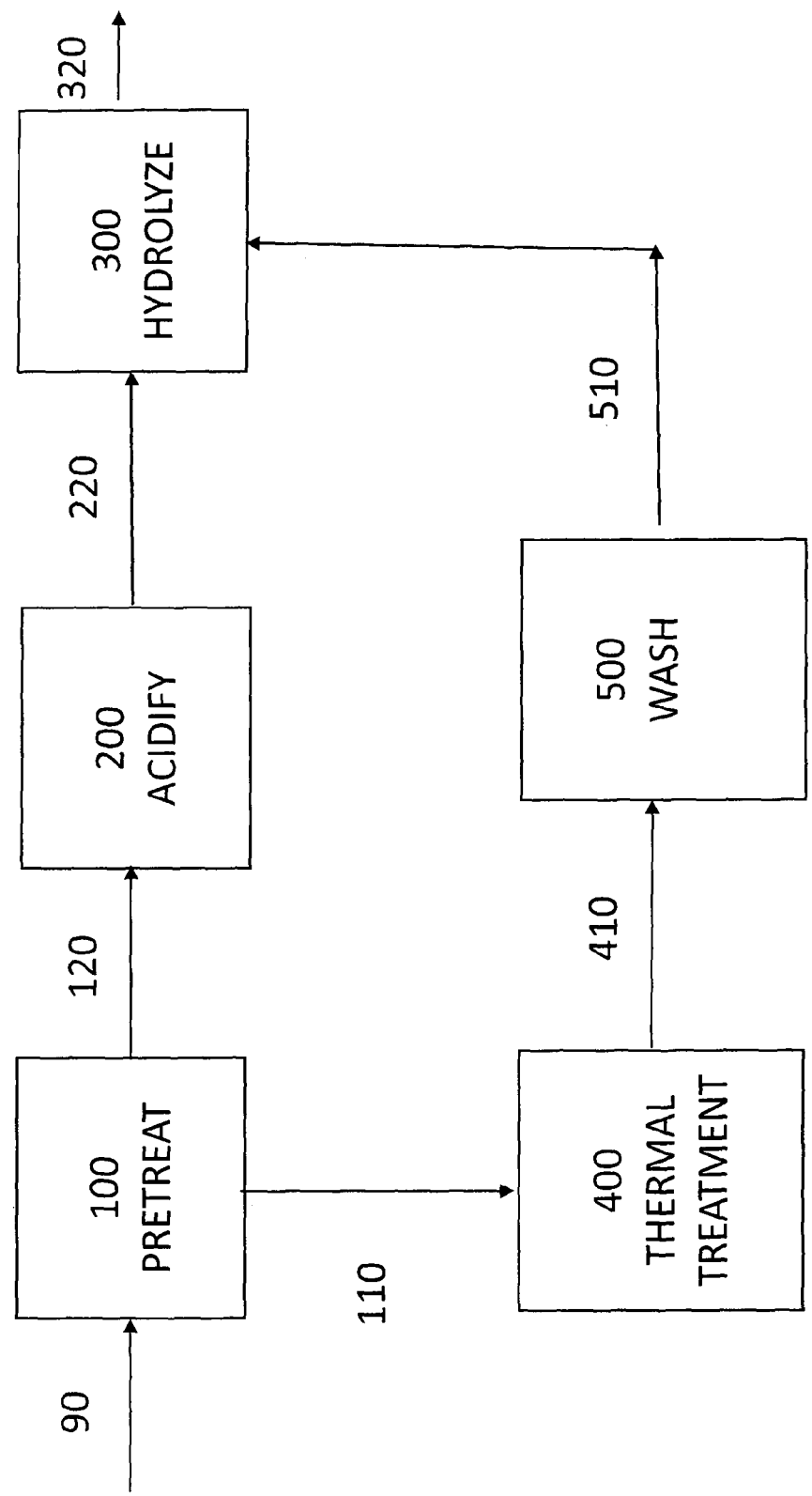
FIG. 3 is a schematic of a third embodiment of the process.

In another embodiment, Embodiment Number 3 (FIG. 3), the process includes a washing step 500 after the thermal pretreatment, but before the hydrolysis step 300. In the washing step, the thermally pretreated solids are rinsed or flushed with water to remove inhibitors that may have formed during the previous treatment, in this case, thermal treatment, and/or unwanted compounds contained in the ligno-cellulosic biomass, which may be detrimental in the acidification or hydrolysis steps. The washed stream 510 is then mixed with the acidic stream 220 for hydrolysis.

Figure 4:
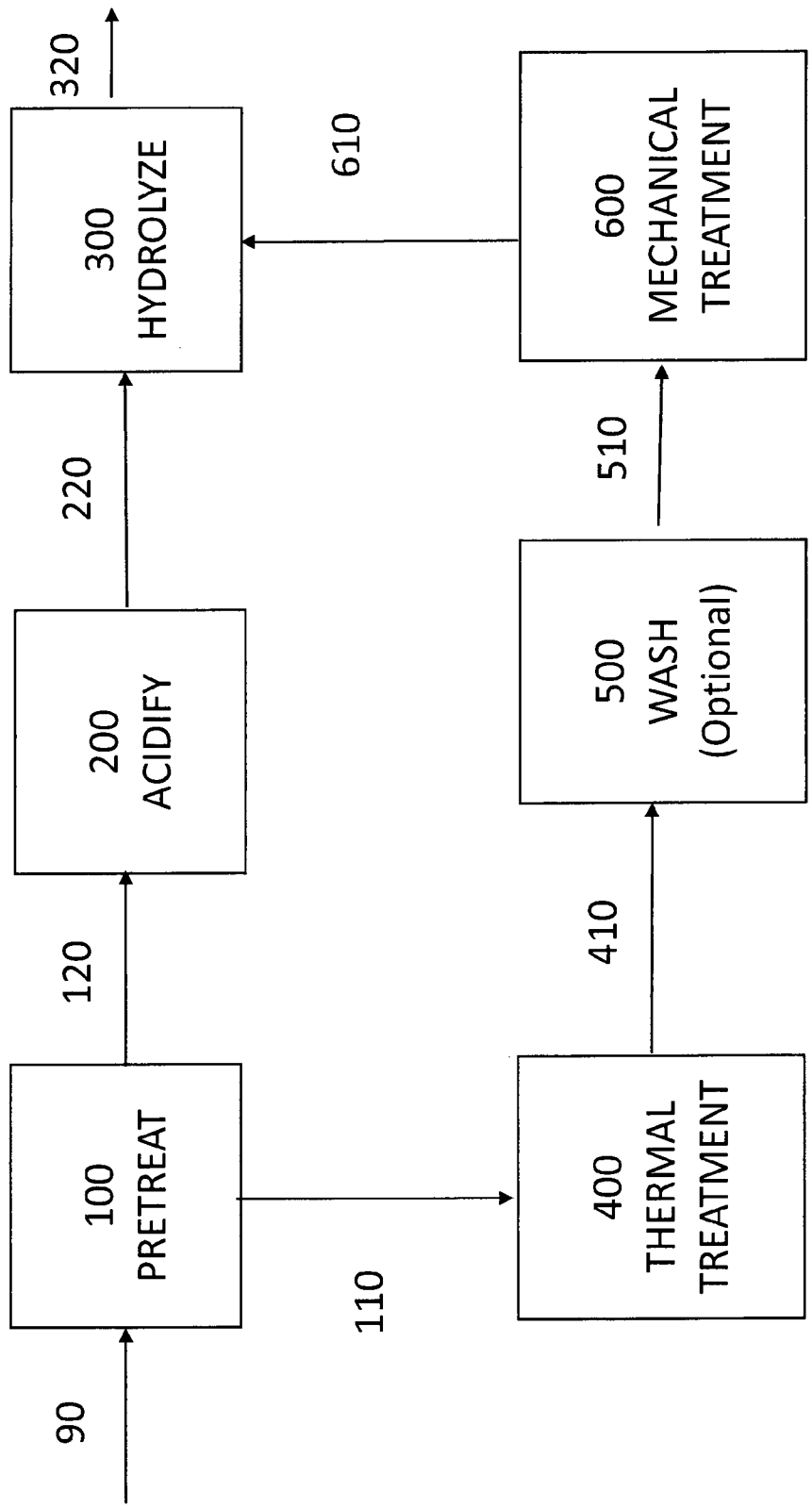
FIG. 4 is a schematic of a fourth embodiment of the process.

In another embodiment, Embodiment Number 4 (FIG. 4), the process may include a wash step 500, and includes a step of fiber shives reduction of the thermally treated solid ligno-cellulosic biomass 600 prior to mixing with the acidic stream 220 for hydrolysis.

Figure 5:
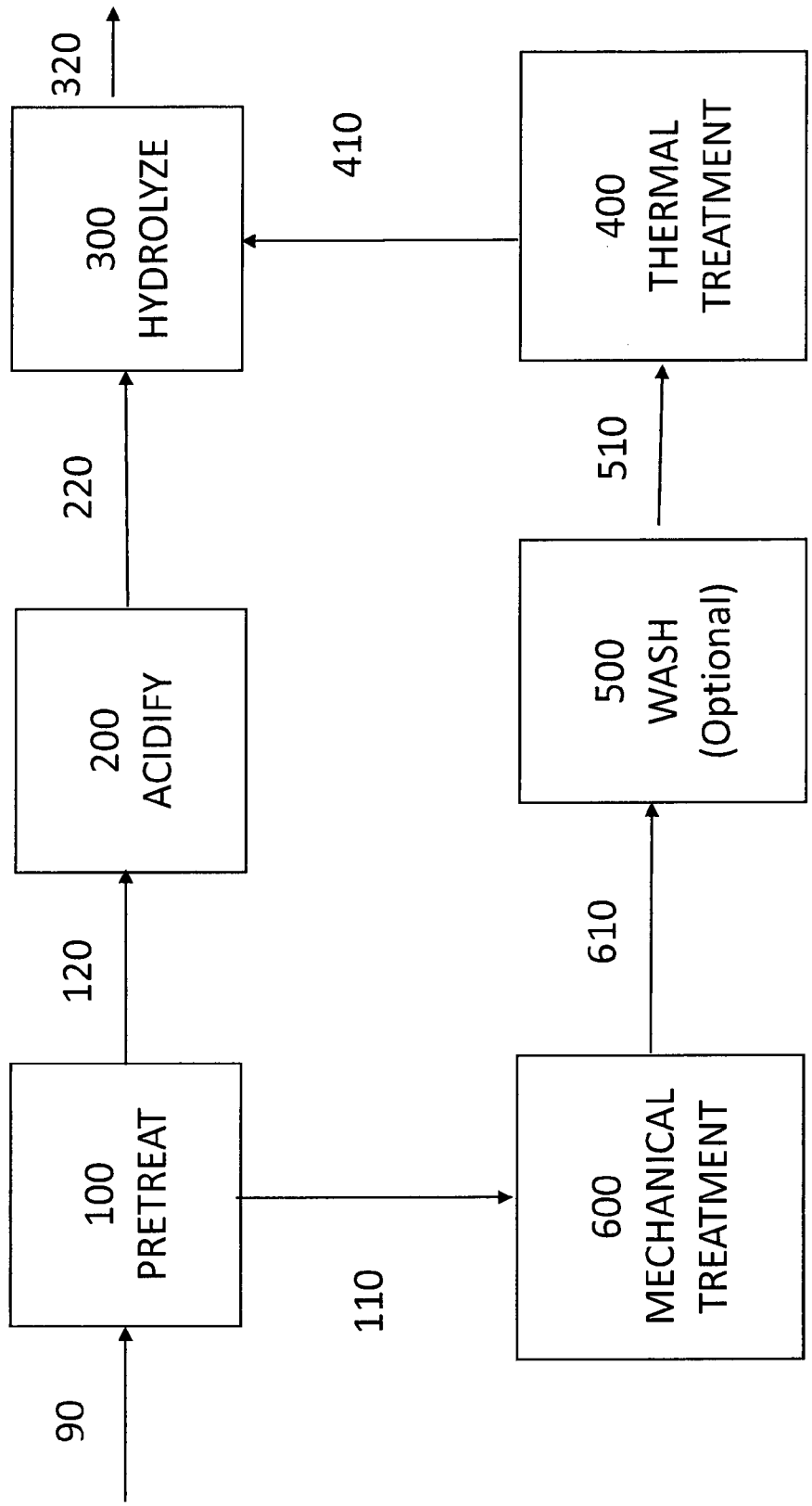
FIG. 5 is a schematic of a fifth embodiment of the process.

In another embodiment, Embodiment Number 5 (FIG. 5), the process is similar to Embodiment 4, however, the order of step 600 and step 400 are reversed. Specifically, the pretreated solid ligno-cellulosic biomass 110 is subjected to fiber shives reduction step 600, and the pretreated solid ligno-cellulosic biomass after fiber shives reduction, after an optional washing step 500, is subjected to thermal treatment 400. The thermally treated ligno-cellulosic biomass, which was subjected to fiber shives reduction before thermal treatment, is then combined with the acidic stream 220 for hydrolysis.

The fiber shives reduction step can occur before or after the thermal treatment, or before the hydrolysis step when no thermal treatment is done.

What inventors discovered is that the thermally treated ligno-cellulosic biomass after fiber shives reduction can be slurried with a carrier liquid to produce a low viscosity slurry, and that the step of reducing fiber shives greatly improves the disclosed process for the hydrolysis of a ligno-cellulosic biomass stream by contacting components of the ligno-cellulosic biomass with very little or no conventional acid or acids. Fiber shives reduction is described in details in a following section.

In one aspect of the present invention, it has been shown that the pretreatment sequence of thermal reaction followed by fiber shives reduction, allows the slurry to form without a hydrolysis catalyst such as enzymes, mineral or organic acids, or bases, almost immediately upon contact of the formed solid with a carrier liquid described below. This does not mean that it is necessary to perform the slurry formation in the absence of enzymes, mineral or organic acids, or bases as with this process, they become optional.

While the carrier liquid may be water, in one embodiment, the carrier liquid is a portion of the acidic stream.

While the creation of the acidic stream can, in practical terms, be done in any manner which increases the concentration of $H^+$ ions. However, the described invention takes advantage of the salt content of the liquid biomass solution. In order to obtain the required acidity for the hydrolysis step, the content of salts in the liquid biomass solution can be reduced via cation exchange while at the same time replacing the cations with $H^+$ ions. While the salts may naturally occur in the liquid biomass solution, they can also be added as part of the pre-treatment processes or prior to or during the creation of the acidic stream.

In various embodiments, the liquid biomass solution may be concentrated following the pretreatment step. This concentration can be done by the removal of water. A 50% removal of water increases the concentration of the non-water species by two. While various concentration increases are acceptable, in one embodiment, at least a two fold increase in the concentration of the xyloligomers in the liquid biomass solution is reached. In one embodiment, at least a fourfold increase in the concentration of the xyloligomers in the liquid biomass solution is reached. In one embodiment, at least a six fold increase in the concentration of the xyloligomers in the liquid biomass solution is reached.

In one embodiment, the acidic stream can also be concentrated. While various concentration increases are acceptable, in one embodiment, at least a two fold increase in the concentration of the xyloligomers in the acidic stream is reached. In one embodiment, at least a fourfold increase in the concentration of the xyloligomers in the acidic stream is reached. In one embodiment, at least a six fold increase in the concentration of the xyloligomers in the acidic stream is reached.

The process of reducing the amount of cations of the salts, called decationization, removes the cations by exchanging them with $H^+$ ions. One way the cations in the solution can be replaced by $H^+$ ions is by using an ion exchange agent, such as an ion exchange resin. The cations can also be exchanged using a membrane. For example, Dupont's Nafion® PFSA Resins can be used as resins in an exchange column or as a membrane through which the solution is passed. These are perfluorinated resins in the sulfonyl fluoride ($-SO_2F$) form.

If a decationizing resin (ion exchange resin) or ion exchange membrane is used, an additional step may be needed for separating at least a portion of the acidic stream from the ion exchange media before subjecting the separated portion to the hydrolysis reaction and temperatures. Preferably, all the ion exchange media is removed from the acidic stream before adding the acidic stream to the hydrolysis reaction conditions.

While the concentration of the natural occurring salts is not so critical, it should be recognized that the amount of salts present influences the amount of $H^+$ ions that can be increased (added to the liquid biomass solution) via ion exchange. The amount of $H^+$ ions also determines the pH of the acidic stream. These salts can be concentrated according to the steps outlined above.

Should the liquid biomass solution not have sufficient salts with cations, one can add a salt or cations in another manner to the liquid biomass solution prior to the creation of the acidic stream, which includes prior to and/or during decationization, and/or after decationization, or combination thereof. Preferably, the salts of Magnesium, Calcium, Sodium, Potassium can be used. Preferably, salts with a monovalent cation are used as the cation will not damage the ion exchange media as much as a bivalent ion. The ion associated with the added salt should be selected so as to benefit, or at least not create problems later in the process or in subsequent process. For example, calcium carbonate is preferred over magnesium sulfate as the sulfur is known to cause problems in later processing.

Should one not want to remove the cations or only remove a small amount of the cations, one may add additional $H^+$ ions to the stream. The amount of $H^+$ ions can be increased via any known means, including the use of acids, electrical current, the addition of hydrogen peroxide, and the use of a membrane; or even in-situ production of the $H^+$ ions. Of course, the practitioner would not use the ion exchange process if one wanted to increase the amount of $H^+$ ions without removing cations. The addition of a small amount of acid may occur at various points in the described process.

Increasing the amount of $H^+$ ions, or protons, in-situ can be accomplished by adding a compound which does not contain $H^+$ ions capable of disassociating in water, but rather catalyses a reaction, or the compound itself reacts, with component(s) already present in the liquid biomass solution. For example, $AlCl_3$ contains no $H^+$ ions. However, when added to the liquid biomass solution, the $AlCl_3$ will react with the water in the liquid biomass solution to form $Al(OH)_3$ and $HCl$, thus creating the $H^+$ ion. In this manner, the amount of the $H^+$ ions are increased without adding $H^+$ ions to the liquid biomass solution.

In the case of decationization, the pH of the decationized, acidic stream becomes lower than the pH of the liquid biomass solution. The pH that can be achieved with decationization depends on the initial cation concentration in the liquid biomass solution, the cations added to the stream, the ion resin exchange capacity, specific velocity through the resin and temperature of exposure.

In one embodiment, the decationization occurs at a temperature in the range of 5° C. to 60° C., for a time sufficient to lower the pH of the liquid biomass solution at least 0.5 units, with 1.0 units being more preferable, and 1.25 being most preferable.

In one embodiment, for a suitable hydrolysis reaction, an acidic stream pH below at least 3.0 is desired. Therefore, in various embodiments, the pH of the acidic stream is selected from the following ranges: less than 3.0; less than 2.5; less than 2.0; less than 1.5; less than 1.39; less than 1.2; and less than 1.0. One of ordinary skill knows that pH has a lower theoretical limit of up to but not including 0, thus each of the above numbers can be expressed as the upper limit of the pH of the acidic stream, with the pH being greater than, but not including, 0.0.

Once the desired pH is reached, the acidic stream is added to the hydrolysis vessel or chamber, either before or after the addition of the pretreated solid lingo-cellulosic biomass, and hydrolysis is initiated by increasing the temperature of the acidic stream to a hydrolysis temperature greater than 80°

C., and in one embodiment, within the range of 80° C. to 200° C. In various embodiments, suitable hydrolysis temperature ranges are selected from the group consisting of 80° C. to 180° C.; 100° 0.0 to 180° C.; 95° C. to 180° C.; 120° C. to 180° C.; and 120° C. to 170° C. The hydrolysis temperature is maintained for a time sufficient to hydrolyze the components (oligosaccharides) to the degree desired. In one embodiment, the time for hydrolysis can be as little as less than 1 second. In various embodiments, it is possible to obtain hydrolysis yields close to 95%, without addition of any acid into the stream, and significantly reducing degradation products.

The phrase acid means homogeneous acid which is a compound that disassociates in water to become at least partially soluble and in so doing donates at least one proton [H+]. While some acid may be added to the process, the amount of acid added should be such that the amount of the $H^+$ ions derived from the acid or acids in combination should be less than 90% of the total amount of $H^+$ ions added to the process, regardless of addition location. In addition to disassociating with water, the acid will react with a base to form a salt. While having less than 90% of the total amount of $H^+$ ions added to the process be derived from an acid or acids is preferred, less than 80% is even more preferred, less than 70% is even more preferred, with less than 25% being another preferred level, with less than 10% being another preferred level, with no amount of $H^+$ ions added to the process being derived from an acid or acids the most preferred; regardless of addition location. In one embodiment, the percentage of the total amount of $H^+$ ions added to the acidic stream derived from an acid or acids is selected from the group consisting of less than 80%, less than 70%, less than 60%, less than 50%, less than 40%, less than 30%, less than 20%, less than 10%, and substantially 0%.

One way to achieve these levels is to add the $H^+$ ions at least in part, if not all, from the group selected from decationization and in situ generation. It has been observed that the lower the pH of the acidic stream, the lower the temperature and time needed for hydrolysis. Because pH is a logarithmic measure, the relationship of lower pH is not believed to be linear with the reduced temperature and time.

In this way, the use of traditionally large amounts of acid or acids used in the hydrolysis step is avoided, allowing the passage from a rather harsh treatment to a totally mild one and the consumption of acid used can be reduced to the amount needed to regenerate the cationic resin (or not used at all). The acid is then recovered in a separate stream and then more easily disposed of.

In one embodiment, the final hydrolysed stream is a cleaner liquid, containing almost exclusively monomeric sugars, low content of salts and low amount of degradation products that could hinder subsequent chemical or biological transformations of the sugars.

Fiber Shives Reduction

The described process utilizes the discovery that a thermally treated ligno-cellulosic biomass can be almost immediately converted to a low viscosity slurry, also known as liquefied to a low viscosity, after a fiber shives reduction step for reducing the amount of long fiber shives. Inventors have found that the low viscosity slurry may be obtained without the use of additives such as mineral acids or bases and without hydrolysis catalyst addition, such as an enzyme or enzyme cocktail.

It is known in the paper and pulp industry that ligno-cellulosic biomass feedstocks are characterized by the content of its particles classified into fibres, fines and fiber shives. Fibres are measured on the basis of their 2 dimensional profile with fibres having a width of 75 μm or less, and a fibre length greater than or equal to 200 μm. Fines are those particles having a width of 75 μm or less, and a fines length less than 200 μm. Geometrically, one can think of a fine as a fibre which has been cut in length. Fiber shives have a shive width greater than 75 μm and can be any length. For the purpose of this specification the shive length can be categorized with a first portion of the fiber shives having a shive length less than 737 μm and a second portion of the fiber shives having a shive length in the range of greater than or equal to 737 μm. Because the width and length describe high aspect ratio particles, the width is less than the length, except in the special case of the circle or square. In the special case when the length and width equal each other the practitioner selects one measurement as the length and arbitrarily therefore, the other measurement as the width.

The 737 μm is selected on the basis of classification of the particle distribution determined by the instrument used in the experiments which gave rise to the disclosed discovery. The sizes of the particles were grouped, with one of the groups having a range of 737-1138 μm. The next group had 1138 as its minimum size. From these groups the graphs were made in figures and determinations made about the effective ranges needed to practice the discovery.

Dimensions of Common NonWood Fibers cited in the Kirk-Othmer Encyclopedia of Chemical Technology, fifth edition, are

| Fibre Source | Mean Length, μm | Mean Diameter, μm | L/D ratio |
| --- | --- | --- | --- |
| Rice straw | 1410 | 8 | 175 |
| Wheat straw | 1480 | 13 | 110 |
| Corn stalk | 1260 | 16 | 80 |
| Cotton stalk | 860 | 19 | 45 |
| Cotton liners | 3500 | 21 | 165 |
| Sugarcane bagasse | 1700 | 20 | 85 |
| Hemp | 20000 | 22 | 1000 |
| Kenaf bast | 2740 | 20 | 135 |
| Kenaf core | 600 | 30 | 20 |
| Seed flax | 27000 | 16 | 1250 |
| Bamboo | 2700 | 14 | 190 |
| Papyrus | 1500 | 12 | 125 |
| Softwood | 3000 | 30 | 100 |
| Hardwood | 1250 | 25 | 50 |

As evident, the average fibre width, as previously defined, is less than or equal to 75 μm.

It is generally viewed that the fiber shives are not a single fibre having the width greater than 75 μm, but bundle of fibres or fibre tangles which combined exhibit a width greater than 75 μm.

This invention is based upon the discovery it is the fiber shives in thermally treated ligno-cellulosic biomass which are responsible for the long enzymatic hydrolysis times, high initial viscosity of slurries from the thermally treated ligno-cellulosic biomass, and the lowered glucose recoveries and yields. This specification demonstrates that by reducing the amount (percentage) of the fiber shives in the thermally treated ligno-cellulosic biomass, the viscosity of the material in a slurry drops dramatically, and there is a significant improvement in sugar yields and recovery during fermentation.

The ability to characterize and fines, fibres and fiber shives is well known in the art and the subject of many industrial standards such as those found in the fiber characterization standards used for all the fiber characterization work in this specification.

Because fiber shives are bundles of fibres, they can be reduced in many ways. First, at least a part of the fiber shives can be removed or separated from the thermally treated ligno-cellulosic biomass. Separation techniques of fiber shives from fibres and fines is well known in the art of natural fibres (e.g. cotton, flax, and others) and also in the paper and pulp industry. Non-limiting examples are the cotton gin and wool carding apparata. Again, not limiting, the separation can occur by bulk density separation, a vibrating bed where the fiber shives separate from the fines and fibres, air elutriation, or even screening, sieving or cyclones. After separation, the fiber shives can be further processing into fibres or fines, and recombined with the thermally treated ligno-cellulosic biomass or re-fed into the thermal treatment process.

The fiber shives can also be reduced by converting them to another form. One method of converting the fiber shives is to apply mechanical forces to the thermally treated ligno-cellulosic biomass to convert the fiber shives to fibres and/or fines. An important consideration is that the difference between a fine and a fibre is the length, as both have a width of less than or equal to 75 μm. The application of mechanical forces to thermally treated ligno-cellulosic biomass is practiced in the art, but always under the belief that the fibres (less than or equal to 75 μm width) must be acted upon. By focusing the application of the mechanical forces upon the fiber shives which are bundles of fibres >75 μm, the amount of work needed is to obtain the benefits mentioned earlier is significantly less than prior art disclosures.

The reason for this reduced work requirement is analogized to yarn which is twisted fibres. It does not take much energy to pull apart a ball of tangled yarn, but it takes much more energy to actually destroy and pull apart the twisted yarn fibre.

The start of the process is the feedstock of thermally treated ligno-cellulosic biomass feedstock. The type of ligno-cellulosic biomass feedstock for the thermal treatment is covered in the feedstock selection section.

In typical conversion of ligno-cellulosic biomass feedstock to ethanol, the ligno-cellulosic biomass is thermally treated prior to enzymatic hydrolysis. Oftentimes this thermal treatment will include acids or bases to increase the liquefaction rate and reduce the hydrolysis time. In many cases the thermal pretreatment includes a steam explosion step.

The thermal treatment is measured by a severity factor which is a function the time and temperature of the thermal treatment. A preferred thermal treatment is described in the thermal treatment section of this specification.

Figure 7:
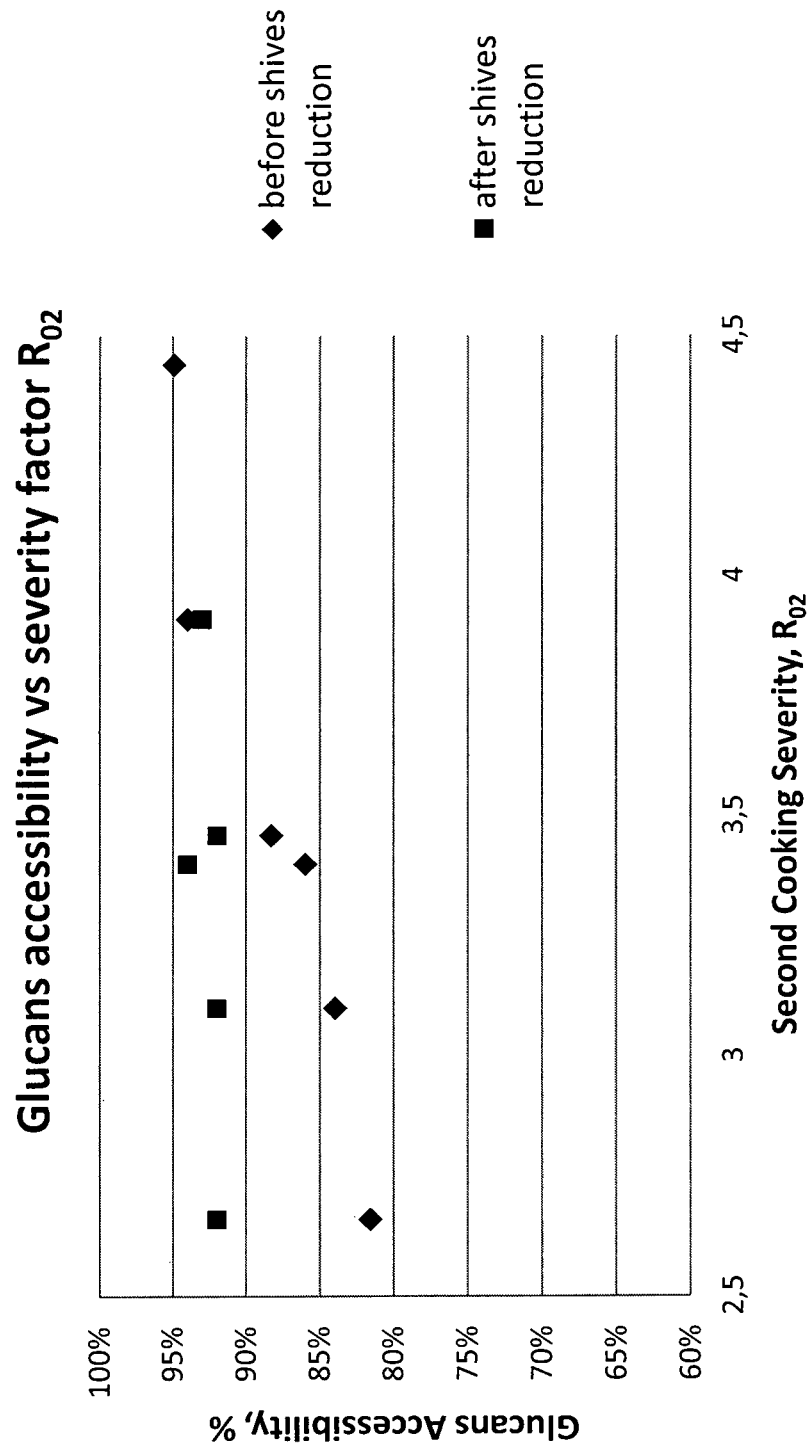
FIG. 7 depicts the glucans accessibility of thermally treated ligno-cellulosic biomass before and after fiber shives reduction at various severity factors of thermal treatment.

The more time of heat exposure, the more the severe the treatment. The higher the temperature of exposure, the more the severe the treatment. The details of calculating the severity factor for this invention are described later. Steam explosion severity factor ($R_{O2}$) is taken as the reference severity factor. However, conventional wisdom holds that the more severe the treatment, the more surface area and cells of the ligno-cellulosic biomass are exposed to enzymes for hydrolysis or further treatment. This is demonstrated in FIG. 7, showing that the glucans become more accessible as the severity factor increases.

Figure 8:
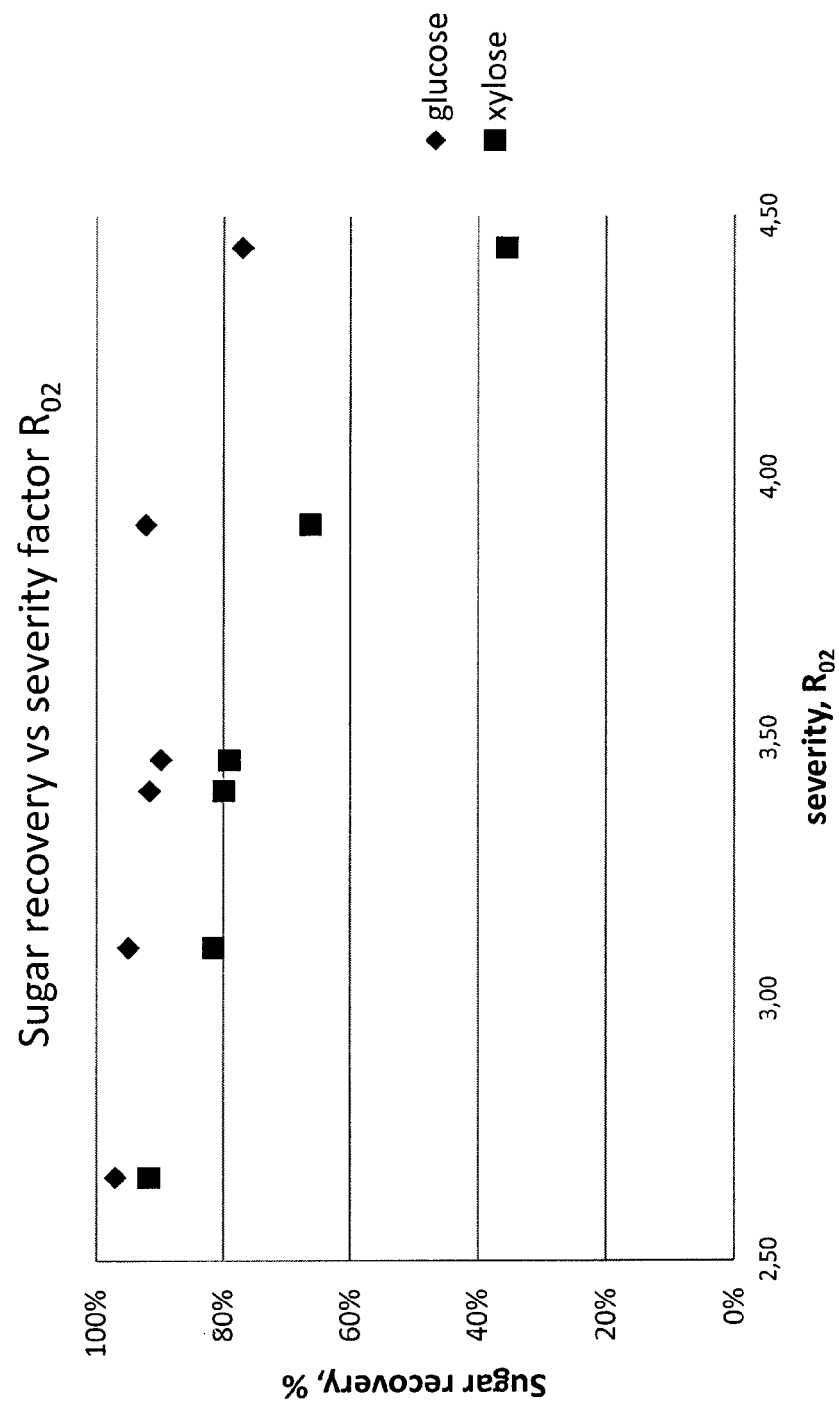
FIG. 8 depicts the glucose and xylose recovery of thermally treated ligno-cellulosic biomass at various severity factors of thermal treatment.

However, as demonstrated in FIG. 8, the amount of glucose and xylose that may be recovered relative to the amount present before the thermal treatment declines at higher severity factors. It is believed that the higher temperature converts or otherwise destroys the sugars. Thus, while the sugars existing in the thermally treated ligno-cellulosic biomass become more available, less sugars exist after severe thermal treatment because the severe temperature/time converts them to sugars degradation products, such as furfural and HMF.

Taking for example, FIG. 8, the points at severity factor 2.66, 97% of the glucose is present after the thermal treatment. In contrast, at a severity factor of 4.44 only 77% is recoverable, or alternatively 23% is destroyed. For xylose, almost 64% is destroyed. However, looking at FIG. 7, for the severity factor of 2.66, only 82% of the glucans are accessible or able to be converted to glucose. Thus, while 97% of the starting amount still exists, only 82% of that can be enzymatically converted. Looking at FIG. 7, severity factor 4.44, 95% of the glucans are accessible but remember from FIG. 8, that only 82% of the starting amount of glucans remains.

What has been discovered is that these inaccessible glucans reside in the fiber shives. When the biomass is processed it is often reduced to width and length that conform to fibres—high aspect ratio as defined in the standard. Usually the thermal treatment of the ligno-cellulosic biomass will create a thermally treated ligno-cellulosic biomass in the physical forms of at least fibres, fines and fiber shives. These physical forms are well known according the definitions described earlier.

Figure 9:
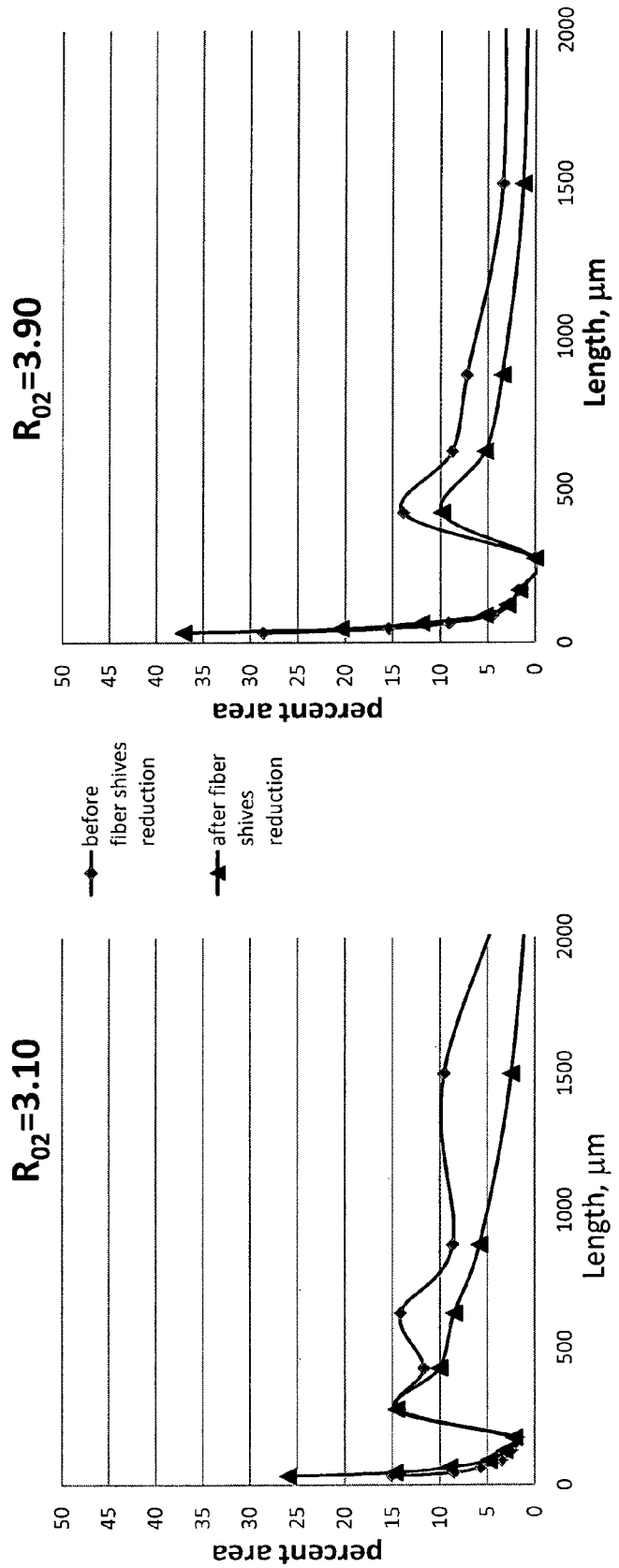
FIG. 9 is fibres and fines distribution of thermally treated ligno-cellulosic biomass before and after fiber shives reduction at two severity factors of thermal treatment.

The fines and fibres (not shives) distribution of thermally treated ligno-cellulosic biomass is shown in FIG. 9. FIG. 9*a*) shows the percent area of each length class relative to the total area of fines, fibres and fiber shives for the severity factor $R_{O2}$ of 3.1. When the severity factor is increased to 3.91, (FIG. 9*b*), it is evident that the percent area of fines has increased (particles of length <200 μm) and the percent area of fibres longer than or equal to 737 μm is reduced. The same considerations hold in the case that population of fines and fibres are considered.

The plots and graphs also show the measurements of the thermally treated ligno-cellulosic biomass after fiber shives reduction, which in this case was passing it through a twin screw extruder at about 35% dry matter content having the screw element design of FIG. 6. The twin screw extruder is also known as a mechanical treatment or the application of mechanical forces on the thermally treated ligno-cellulosic biomass. One of ordinary skill could easily obtain this design from the manufacturer listed.

The dominant role of the fiber shives is evidenced by seeing that first, according to FIG. 9, the thermally treated ligno-cellulosic biomass after fiber shives reduction through the extruder has a reduced percent area of long fibres for both the low and high severity factors of 3.1 and 3.91. However, for the low severity factor of 3.1, the conversion of fiber shives improved the glucan accessibility from 84 to 93 percent (FIG. 7). Again, the same considerations hold in the case that population of fibres and fiber shives are considered. While at the high severity of 3.91, there was substantially no improvement in the glucan accessibility. Were the long fibres responsible for accessibility, the accessibility of the glucans for the thermally treated ligno-cellulosic biomass should have been less than 94% and the reduction of the percent area of long fibres (or equivalently the population of long fibres) during the extrusion (application of mechanical forces) should have caused an increase in the accessibility. The accessibility did not increase establishing that it is not the conversion of fibres to fines that causes the increased accessibility.

Figure 10:
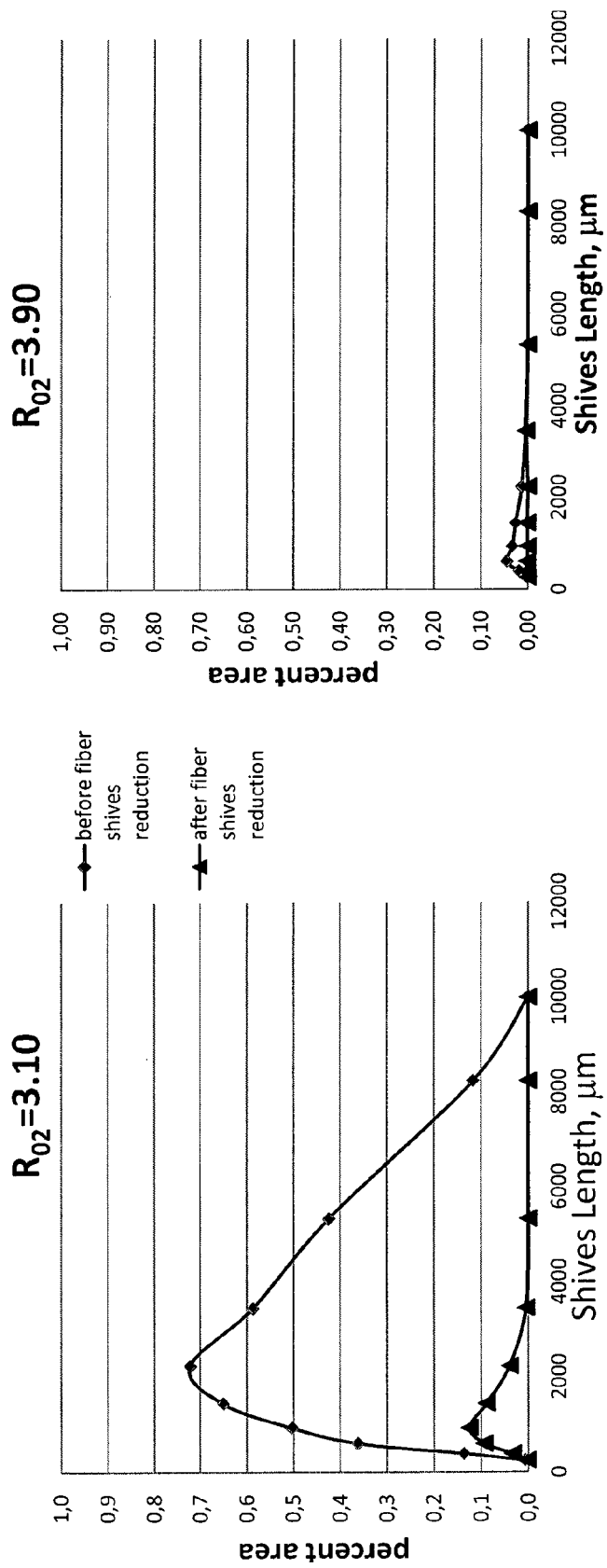
FIG. 10 is the fiber shives distribution of thermally treated biomass before shives reduction and the thermally treated biomass after shives reduction at two severity factors of thermal treatment.
Figure 11:
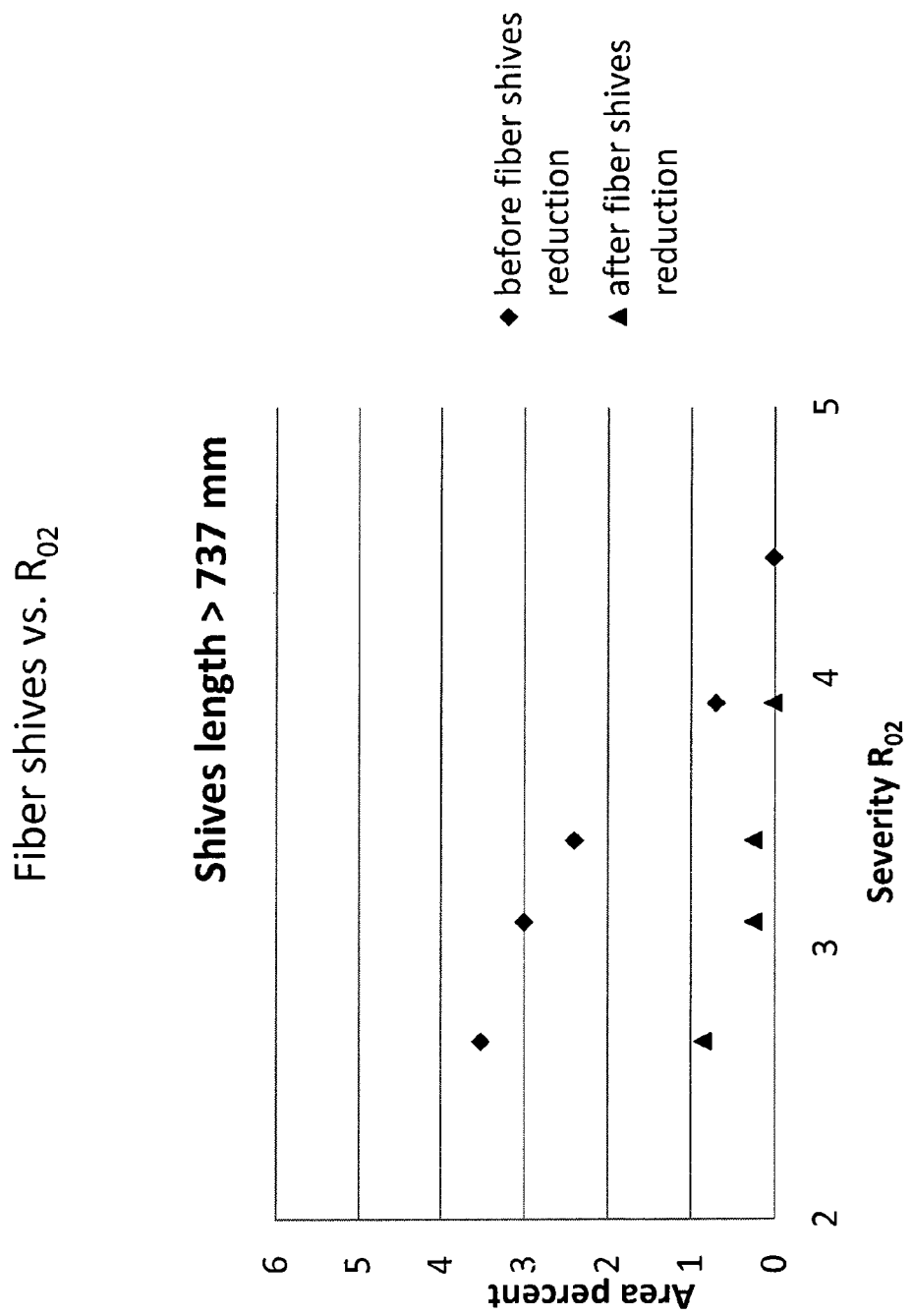
FIG. 11 is the fiber shives content of thermally treated ligno-cellulosic biomass before and after fiber shives reduction as a function of the severity factor of thermal treatment.

The role of the fiber shives is shown in FIG. 10, which contains the percent area distribution of fiber shives of two samples prepared at low severity factor ($R_{O2}$=3.10, FIG. 10*a*) and high severity factor ($R_{O2}$=3.90, FIG. 10*b*), before fiber shives reduction and after fiber shives reduction. The sample at low severity before fiber shives reduction contains a remarkable amount of fiber shives and the mechanical treatment reduces the amount of fiber shives in the sample at low severity, while the sample at high severity has already a small amount of fiber shives before fiber shives reduction. FIG. 11 reports the total percent area of fiber shives having a fiber shives length greater than 737 µm. The percent area of fiber shives of the sample at low severity is reduced from 3.5. % to less than 1% by the fiber shives reduction. However, for the high severity thermally treated ligno-cellulosic biomass, fiber shives percent area is already less than 1% before fiber shives reduction. Thus, there is the conclusion that once the fiber shives are below a certain threshold, their removal does not impact the properties in a measurable way. Therefore, the percent area of the fiber shives having a shive length greater than or equal to 737 µm relative to the total area of fiber shives, fibres and fines of the thermally treated ligno-cellulosic biomass before fiber shives reduction is greater than a value selected from the group consisting of 1%, 2%, 3% and 4% and the percent area of the fiber shives having a shive length greater than or equal to 737 µm relative to the total area of fiber shives, fibers and fines of the thermally treated ligno-cellulosic biomass after fiber shives reduction is less than a value selected from the group consisting of 1%, 0.5, 0.25%, 0.02%, and 0.1%.

In a preferred embodiment, the percent area of the fiber shives having a shive length greater than or equal to 737 µm relative to the total area of fiber shives, fibers and fines of the thermally treated ligno-cellulosic biomass after fiber shives reduction is greater than 0, and less than a value selected from the group consisting of 1%, 0.5, 0.25%, 0.02%, and 0.1%, that is some long fiber shives are still present in the thermally treated ligno-cellulosic biomass after fiber shives reduction.

The total area of fiber shives, fibres and fines is measured using automated optical analysis which determines the area of the fiber shives, the area of the fibres and the area of fines. The proper machine, as described in the experimental section, will often provide the area of each individual class, as well as the area of each class as a percent of the total area of the sum of the classes. In the event the machine does not do the math, one of ordinary skill should be able to calculate the percent area knowing the areas, or the area knowing the total area and percent of each class measured.

In any event, the effect of the shives reduction should be such that the percent area of the fiber shives having a shive length greater than or equal to 737 µm relative to the total area of fiber shives, fibres and fines of the thermally treated ligno-cellulosic biomass after fiber shives reduction is less than a value selected from the group consisting of 5%, 10%, 20%, 30%, 40%, 50%, 60% and 70% of the percent area of the fiber shives having a shive length greater than or equal to 737 µm relative to the total area of fiber shives, fibers and fines of the thermally treated ligno-cellulosic biomass before fiber shives reduction.

Because the fiber shives are comprised of fibre bundles and agglomerated fibres, a reduced amount of energy is needed as compared to the prior art. As described in the experimental section only 0.1 to 0.2 Kw-h/kg on a wet basis or 0.25 to 0.50 Kw-h/kg on a dry matter basis was used to achieve the effects. Thus the preferred amount of work, or energy, imparted to the thermally treated ligno-cellulosic biomass is preferably less than a number selected from the group consisting of 500 Wh/Kg, 400 Wh/Kg, 300 Wh/Kg, 200 Wh/Kg, 100 Wh/Kg, per kg of the thermally treated ligno-cellulosic biomass on a dry basis. It is preferable that at least a part of the fiber shives reduction is done by applying mechanical forces to the thermally treated ligno-cellulosic biomass, and all the work applied in form of mechanical forces on the thermally treated ligno-cellulosic biomass is less than 500 Wh/Kg per kg of the thermally treated ligno-cellulosic biomass on a dry basis. It is even more preferable that all the work done by all the forms of mechanical forces on the thermally treated ligno-cellulosic biomass is less than a value selected from the group consisting of 400 Wh/Kg, 300 Wh/Kg, 200 Wh/Kg, 100 Wh/Kg, per kg of the thermally treated ligno-cellulosic biomass on a dry basis.

The application of mechanical forces to the thermally treated ligno-cellulosic biomass should be a mechanical process or sub-processes which applies work to the thermally treated ligno-cellulosic biomass and reduces the number of fiber shives longer than or equal to 737 µm during the fiber shives reduction. Mechanical forces applying work are distinct from chemical processes which may dissolve the fiber shives, for example. The type of forces or work applied as a mechanical force is shear, compression, and moving. It should be appreciated that the mechanical treatment may be a conversion process where the application of mechanical forces converts at least a portion of the fiber shives in the thermally treated ligno-cellulosic biomass to fibres or fines that remain part of the output. One class of machines for applying this type of work in a mechanical manner are those machines which apply shear such as an extruder, a twin screw extruder, a co-rotating extruder, a counter-rotating twin screw extruder, a disk mill, a bunbury, a grinder, a rolling mill, a hammer mill.

Preferably, the mechanical energy applied to the thermally treated ligno-cellulosic biomass is not mechanical energy derived from free-fall or gravity mixing.

In any case, it is noted the amount of work applied to the thermally treated ligno-cellulosic biomass for a given amount of time should be greater than the amount of work that can be provided by the forces of gravity or free fall mixing in that same period. One way to measure this is to consider the period of time in which the fiber shives are reduced to be the called fiber shives reduction time. The amount of work applied to the thermally treated ligno-cellulosic biomass during the fiber shives reduction time is preferably greater than the amount of work which can be applied to the thermally treated ligno-cellulosic biomass by free fall mixing or gravity. One embodiment will have no work applied in the form of free fall mixing or gravity during the shives reduction.

The fiber shives reduction time is preferably in the range of 0.1 to 30 minutes. While the fiber shives reduction time can be any positive amount less than 12 hours, less than 6 hours is more preferable, with less than 3 hours even more preferred and less than 1 hour more preferred, and less than 30 minutes being more preferable with less than 20 minutes being most preferred. In the case of an extruder, the preferred fiber shives reduction time is in the range of 0.1 to 15 minutes.

One of ordinary skill knowing that the forces are to be applied to fibre shives which on the average are 2 to 5 times the width of the fibre (less than or equal to 75 µm, averaging of 30-40 µm versus the fiber shives of 130-180 µm width) can easily adjust the apparatus. The twin screw extruder applies mechanical work in the forms of shear, compression and movement down the barrel of the screw. For a twin screw extruder one keeps the flights and distances further apart, as tighter distances applying forces to fibres are only wasted. In the experiments conducted in this specification, a conventional twin screw extruder for PET resins was used with no special screw as described in the prior art. For mills or blades, one sets the distance between the two parts creating the force for the particles having width of 130-180 µm, not the particles less than or equal to 75 µm.

The simplest example of these machines are grist mills where two stones are rotated with a space between them. The space between the stones sets the size. One of ordinary skill would set the stones a distance apart to apply the force to particles having a width of >75 µm, with the fibres having a width of less than 75 µm passing between the stones with little or no work applied to these smaller particles. A disk mill is of the similar operation as it is the space between the disks which sets the application of the force.

Figure 12:
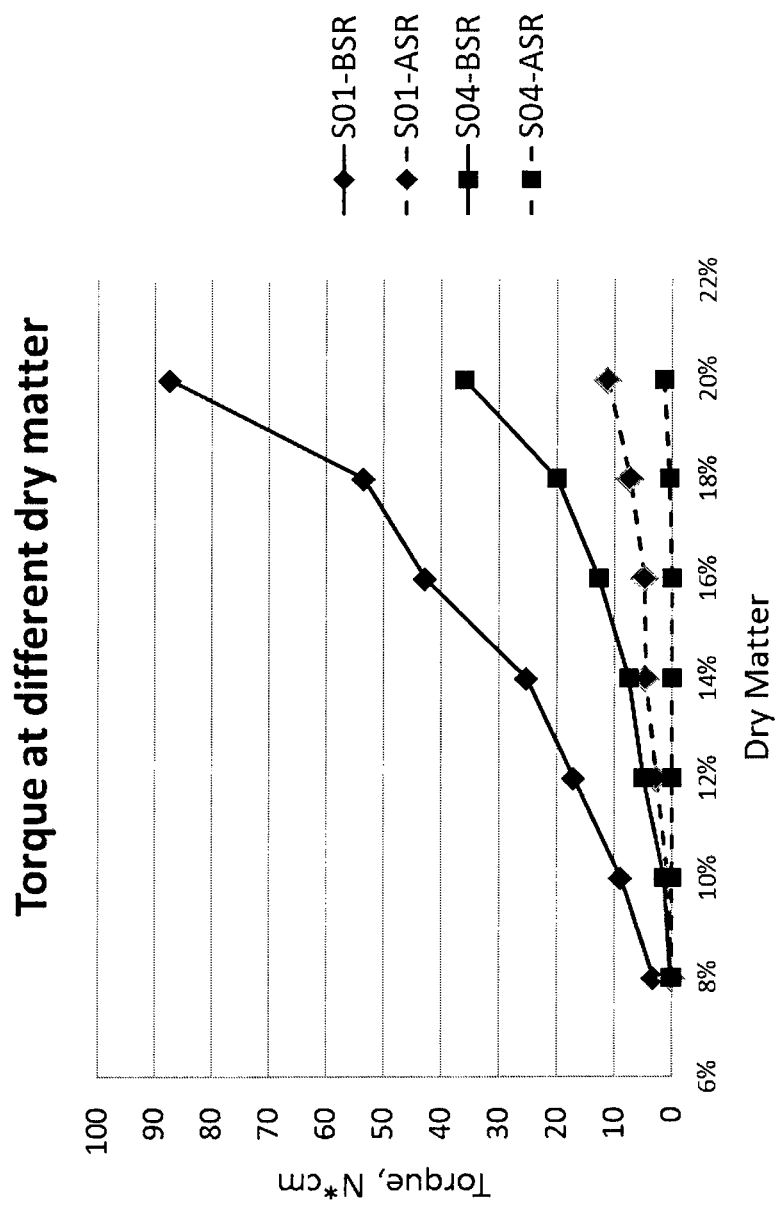
FIG. 12 plots the torque of slurries of various experimental runs at different dry matter contents in the slurry.

An additional feature it has been discovered, that once the fiber shives level is low enough, the thermally treated ligno-cellulosic biomass after fiber shives reduction will have much lower viscosity than the thermally treated ligno-cellulosic biomass when both are made into a slurry of water at the same dry matter content. FIG. 12 demonstrates this, at 20% dry matter the S01 (produced at a steam explosion severity factor of 2.66)) thermally treated material before fiber shives reduction needed a torque of 87 N-cm, while the thermally treated ligno-cellulosic biomass after shives reduction, needed only 11 N-cm.

Figure 13:
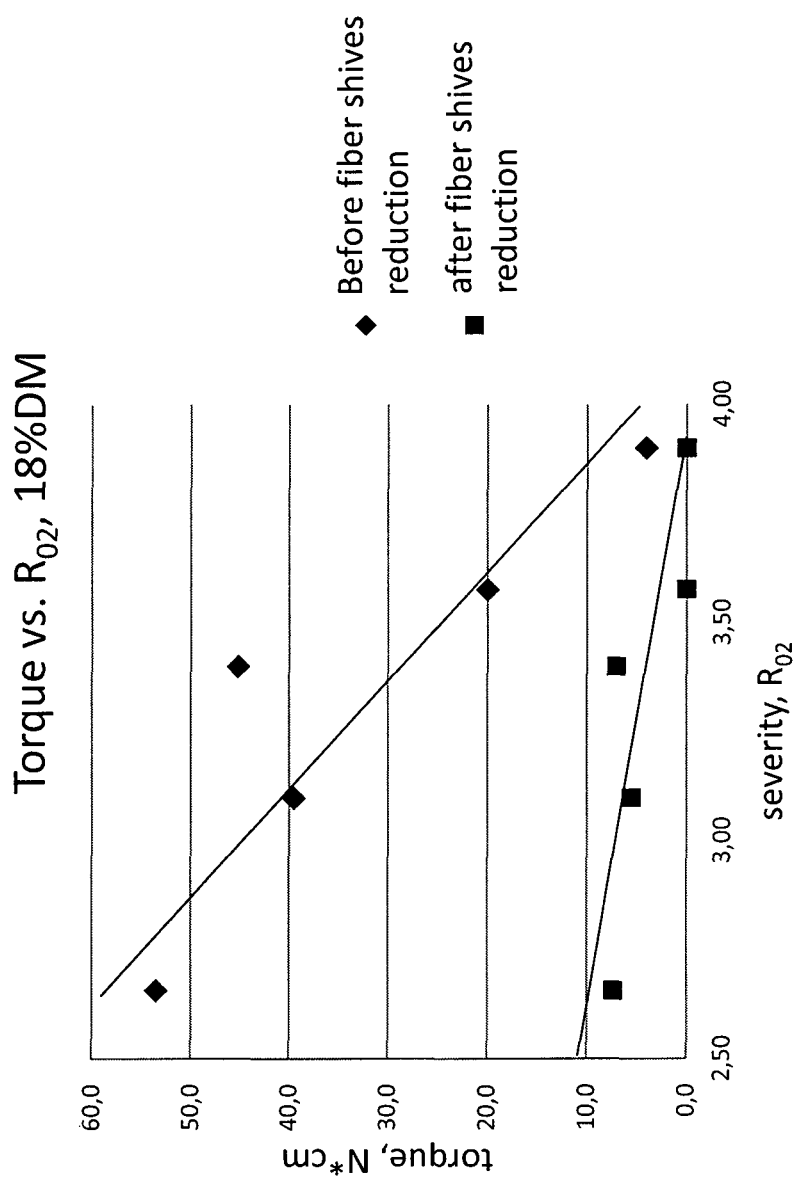
FIG. 13 plots the torque of slurries made from 18% dry matter content of the thermally treated ligno-cellulosic biomass before and after fiber shives reduction as a function of the severity factor of thermal treatment.

FIG. 13 shows the torque needed to agitate a slurry at 18% dry matter of thermally treated materials prepared at different severity factor, before and after fiber shives reduction. The torque decreases by increasing the severity factor, as the samples at low severity factor contain a bigger amount of fiber shives (FIG. 11). For each thermally treated material, the torque decreases by reducing the fiber shives by means of a mechanical treatment, but the effect is remarkably more evident in samples at low severity factor, which contains more fiber shives.

This slurry effect is especially critical as it can be can be done without hydrolysis, meaning that the low viscosity stream can be passed over an immobilized enzyme bed for enzymatic hydrolysis, or passed over a ion exchange resin for cationic exchange and subsequent "acid" hydrolysis.

This property is especially useful when exposing the material to enzymatic hydrolysis. In FIG. 10, the thermally treated ligno-cellulosic biomass before fiber shives reduction and the thermally treated ligno-cellulosic biomass after shives reduction were "slurried" into water with enzymes added at the arrow. It took 2+ hours after the enzymes were added for the viscosity of the thermally treated ligno-cellulosic biomass before fiber shives reduction to approach that of the thermally treated ligno-cellulosic biomass after fiber shives reduction. Thus, the process can be further characterized in that the output of thermally treated ligno-cellulosic biomass after fiber shives reduction is characterized by having a viscosity of a slurry of the thermally treated ligno-cellulosic biomass after fiber shives reduction in water less than the viscosity of a slurry of the thermally treated ligno-cellulosic biomass before fiber shives reduction in water, wherein the viscosities are measured at 25° C., at a shear rate of 10 s$^{-1}$ and at a dry matter content of 7% by weight of each slurry.

The process can be further characterized in that the thermally treated ligno-cellulosic biomass after fiber shives reduction is characterized by having a viscosity of a slurry of the thermally treated ligno-cellulosic biomass after fiber shives reduction in water less than a value selected from the group consisting of 0.1 Pa s, 0.3 Pa s, 0.5 Pa s, 0.7 Pa s, 0.9 Pa s, 1.0 Pa s, 1.5 Pa s, 2.0 Pa s, 2.5 Pa s, 3.0 Pa s, 4 Pa s, 5 Pa s, 7 Pa s, 9 Pa s, 10 Pa s, wherein the viscosity is measured at 25° C., at a shear rate of 10 s$^{-1}$ and at a dry matter content of 7% by weight of the slurry of the thermally treated ligno-cellulosic biomass after fiber shives reduction in the water.

The process can further comprise a slurry step, wherein the thermally treated ligno-cellulosic biomass before, during or after fiber shives reduction is dispersed into a liquid carrier, preferably comprising water or aqueous, to create a slurry stream. The slurry stream preferably has a viscosity less than a value selected from the group consisting of 0.1 Pa s, 0.3 Pa s, 0.5 Pa s, 0.7 Pa s, 0.9 Pa s, 1.0 Pa s, 1.5 Pa s, 2.0 Pa s, 2.5 Pa s, 3.0 Pa s, 4 Pa s, 5 Pa s, 7 Pa s, 9 Pa s, 10 Pa s, wherein the viscosity is measured at 25° C., at a shear rate of 10 s$^{-1}$ and at a dry matter content of 7% by weight of the slurry stream. The slurry stream will preferably have a dry matter content less than 100% but greater than a value selected from the group consisting of 5%, 7%, 8%, 10%, 12%, 15%, 18%, 20%, 25%, 30%, 35%, and 40%.

Because this slurry stream having this viscosity can be made without the use of hydrolysis catalysts such as enzymes, acids or bases, thus, the inventors have discovered an entirely new article of manufacture which is a slurry comprising water, soluble sugars, solid lignin, solid cellulose, which has a dry matter content in the range of 20 to 80% by weight of the total amount of the slurry and is void of or substantially void of a hydrolytic catalyst such as an enzyme or enzymes. Other preferable ranges of dry matter range are 25 to 80% by weight, with 30 to 80% by weight even more preferable. In some instances the dry matter range will have an upper limit of 70% by weight, with 60% less preferable and 40% even less preferable.

The torque of the slurry comprising the thermally ligno-cellulosic biomass after fiber shives reduction at 10 minutes after the addition of the solvent is less than the torque of a mixture of the thermally treated ligno-cellulosic biomass before fiber shives reduction when using the same amount and composition of the solvent measured 10 minutes after the solvent has been added to the thermally pre-treated ligno-cellulosic biomass before fiber shives reduction and under the same mixing condition when both torque measurements are at 25° C. Preferably the torque of the thermally treated ligno-cellulosic biomass after fiber shives reduction should be at least less than 50% of the torque of the thermally treated ligno-cellulosic biomass before fiber shives reduction, with at least less than 40% even more preferred, with at least less than 30% even more preferred.

It is also preferable that the solvent creating the slurry is not pure recycled process water as offered in WO 2011/044292 and WO 2011/044282, but to use liquid containing solubles and possibly insolubles from a hydrolysis reactor or alternatively use materials derived from the stillage after the hydrolyzed material has been fermented. In another embodiment, the solvent comprises liquids produced during the thermal treatment, said liquids comprising monomeric and oligomeric sugars which have been solubilized as an effect of the thermal treatment. While the addition point in WO 2011/044292 and WO 2011/044282 is at the end of a compounder, the liquid comprising the hydrolysis products of a similarly, if not same, ligno-cellulosic biomass, also considered a solvent in this specification is used to slurry the thermally treated ligno-cellulosic biomass after fiber shives reduction.

The thermally treated ligno-cellulosic biomass, either before and after fiber shives reduction, comprises glucans, xylans and lignin. As the thermal treatment is preferably conducted so as to avoid the removal of all or great amount of the lignin of the starting ligno-cellulosic biomass feedstock, the percent lignin content of the thermally pretreated ligno-cellulosic biomass is greater than 15% by weight on a dry basis. Depending on the feedstock selection and the specific thermal pretreatment, the percent lignin content of the thermally pretreated ligno-cellulosic biomass may be greater than 20%, preferably greater than 25%, more preferably greater than 30%, even more preferably greater than 40%, and most preferably greater than 50%.

The thermally treated ligno-cellulosic biomass, either before and after fiber shive reduction may be further characterized by the ratio of the amount of glucans of the thermally treated ligno-cellulosic biomass to the amount of lignin of the thermally treated ligno-cellulosic biomass, which may be greater than a value selected from the group consisting of 1.5, 1.8, 2.0, 2.2, and 2.5.

Figure 14:
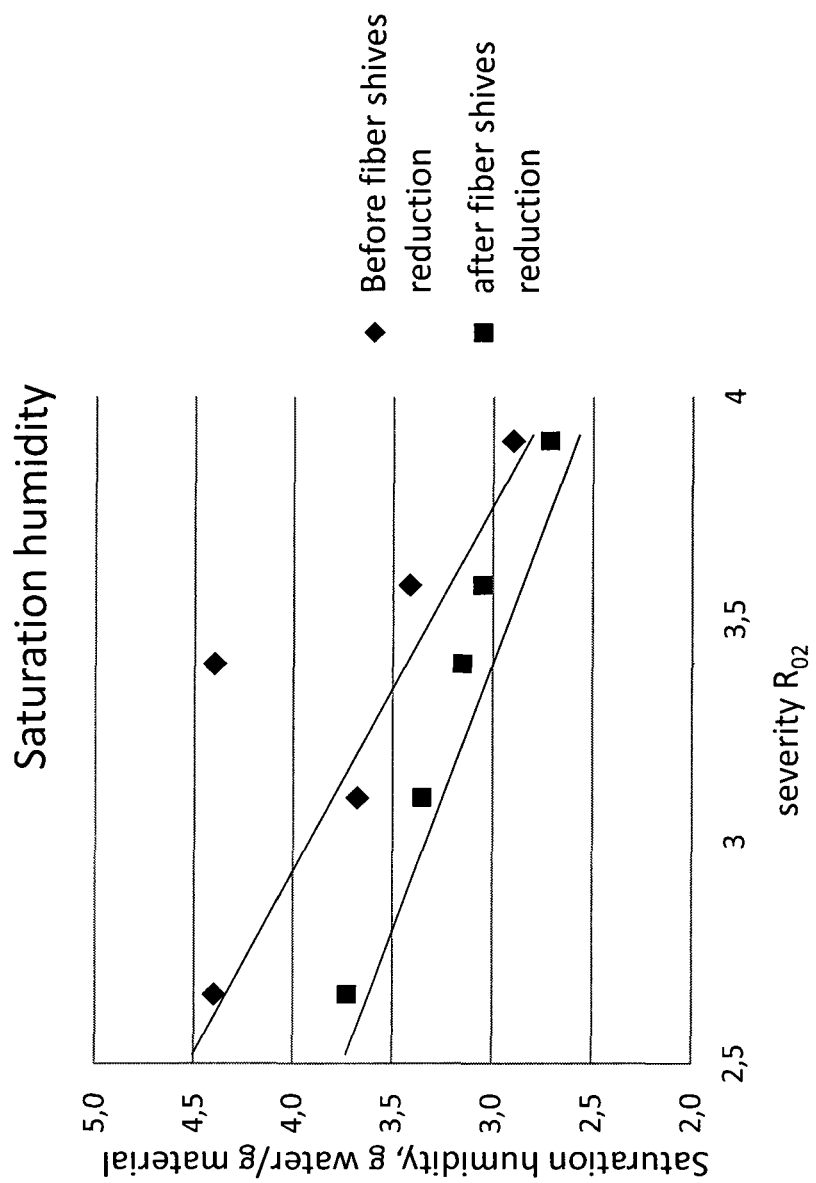
FIG. 14 plots the saturation humidity of thermally treated ligno-cellulosic biomass before and after fiber shives reduction at different severity factors of thermal treatment.

The process can be further characterized, as demonstrated in FIG. 14, by the saturation humidity of the thermally treated ligno-cellulosic biomass after fiber shives reduction and the thermally treated ligno-cellulosic biomass before fiber shives reduction because the saturation humidity of the thermally treated ligno-cellulosic biomass after fiber shives reduction is less than the saturation humidity of thermally treated ligno-cellulosic biomass.

It can be said that thermally treated ligno-cellulosic biomass after fiber shives reduction has a first saturation humidity, and the thermally treated ligno-cellulosic biomass before fiber shives reduction has a second saturation humidity, and the first saturation humidity is less than the second saturation humidity.

In fact, when compared to each other the saturation humidity of the thermally treated ligno-cellulosic biomass after fiber shives reduction is less than a value selected from the group consisting of 20%, 30%, 40%, 50%, 60%, 70% and 80% of the thermally treated ligno-cellulosic biomass before fiber shives reduction.

In terms of output characterization, the saturation humidity of the thermally treated ligno-cellulosic biomass after fiber shives reduction is preferably less than a value selected from the group consisting of 5.5, 5.0, 4.5, 4.0, 3.5, 3.0, 2.5, 2.0, 1.5, and 1.0 g/g expressed as gram of water per gram of thermally treated ligno-cellulosic biomass after fiber shives reduction on a dry basis.

In terms of feedstock selection it is preferable that the saturation humidity of the thermally treated ligno-cellulosic biomass before fiber shives reduction is less than a value selected from the group consisting of 6.0, 5.5, 5.0, 4.5, 4.0, 3.5, 3.0, and 2.5 g/g, expressed as gram of water per gram of thermally treated ligno-cellulosic biomass ligno-cellulosic biomass on a dry basis.

The thermally treated ligno-cellulosic biomass preferably has a dry matter content of at least 20% by weight of the total content of the thermally treated ligno-cellulosic biomass. With the dry matter content of the thermally treated ligno-cellulosic biomass preferably in the range of at least a value selected from the group consisting of 25%, 30%, 35%, and 40% by weight of the total content of the thermally treated ligno-cellulosic biomass to less than 80% by weight of the total content of the thermally treated ligno-cellulosic biomass.

Xylose recovery is the percent ratio between the total amount of xylans in the thermally treated ligno-cellulosic biomass before fiber shives reduction (as xylose equivalents calculated including insoluble xylans, xylo-oligomers, xylobiose and xylose present in both the solid and liquid of the ligno-cellulosic biomass) and the total amount of xylans (converted in xylose equivalents) present in the raw material before the thermal treatment. The complementary to 100% of the xylose recovery represents therefore the total amount of xylans degradation products as an effect of the thermal treatment.

In the case when the fiber shives reduction converts fiber shives to fines or fibres, the amount of xylose equivalents in the final composition after fiber shives reduction is the same as the amount of xylose equivalents in the thermally treated material before fiber shives reduction.

In terms of xylose recovery, the thermally treated ligno-cellulosic biomass before fiber shives reduction may preferably have a xylose recovery greater than a value selected from the group consisting of 85%, 90%, 92%, 95%, and 98%.

Glucose recovery is the percent ratio between the total amount of glucans in the thermally treated ligno-cellulosic biomass before fiber shives reduction (as glucose equivalents calculated including insoluble glucans, gluco-oligomers, cellobiose and glucose present in both the solid and liquid of the ligno-cellulosic biomass) and the total amount of glucans (converted in glucose equivalents) present in the raw material before the thermal treatment. The complementary to 100% of the glucose recovery represents therefore the total amount of glucans degradation products as an effect of the thermal treatment.

In terms of glucose recovery, the thermally treated ligno-cellulosic biomass before fiber shives reduction preferably has a glucose recovery greater than a value selected from the group consisting of 90%, 92%, 95%, and 98%. The glucans accessibility of the thermally treated ligno-cellulosic biomass before fiber shives reduction is preferably greater than a value selected from the group consisting of 80%, 85%, 88%, 90%, 92%, 95%, and 98% or the glucans accessibility can be lower than a value selected from the group consisting of 75%, 78%, 80%, 82%, 85%, 88% and 91%.

Like xylose, in the case when the fiber shives reduction converts fiber shives to fines or fibres, the amount of glucose equivalents in the final composition after fiber shives reduction is the same as the amount of glucose equivalents in the thermally treated material before fiber shives reduction.

In terms of glucans accessibility, the thermally treated ligno-cellulosic biomass after fiber shives reduction has a first glucans accessibility and the thermally treated ligno-cellulosic biomass before fiber shives reduction has a second glucans accessibility and the first glucans accessibility is greater than the second glucans accessibility.

As the experiments in this specification were done without the addition of acids or bases, it can be said that the thermally treated ligno-cellulosic biomass may preferably be free of added ionic species such as acids or bases, which are species added to the thermally treated ligno-cellulosic biomass after harvesting, i.e. not part of its natural composition. Thus the thermally treated ligno-cellulosic biomass is free of an added acid and/or added base. It is preferred then that if there any ionic groups that the amount and type of ionic groups present in the ligno-cellulosic feedstock are the amounts and types of the respective ionic groups that are not derived from the group consisting of mineral acids, organic acids and organic bases.

The same is true of the process itself of thermal treatment and mechanical treatment as these steps can be conducted in the absence of an added acid and/or added base.

In particular, preferably the thermally treated ligno-cellulosic biomass does not contain sulfur. In the case that sulfur is already present in the ligno-cellulosic biomass feedstock, the percent amount of sulfur by weight in the thermally pretreated ligno-cellulosic biomass on a dry basis is preferably less than a value selected from the group consisting of 4%, 3%, 2, and 1%.

The thermal treatment preferably have a severity ($R_O$) lower than a value selected from the group consisting of 4.0, 3.75, 3.5, 3.25, 3.0, 2.75 and 2.5. The preferred thermal treatment will also comprise a steam explosion step.

In a preferred embodiment, the thermal treatment is conducted at low severity factor, so as to enhance the fiber shives reduction effects in the thermally treated ligno-cellulosic material after fiber shives reduction with respect to the thermally treated ligno-cellulosic biomass before fiber shives reduction. Moreover, the low severity thermal treatment will be more convenient, as it requires less thermal energy. As a consequence the low severity thermally treated ligno-cellulosic biomass after fiber shives reduction will have some peculiar properties.

It is known in the art that a severe thermal treatment has a more remarkable effect on xylans, in terms of solubilization and/or degradation, than on glucans. Thereby, the low severity thermally treated ligno-cellulosic biomass will contain more xylans, with respect to glucans, than a high severity thermally treated ligno-cellulosic biomass, as evident in FIG. 8. This is evident in the graph of FIG. 8. The fiber shives reduction step is conducted substantially to not change the chemical composition of the thermally treated ligno-cellulosic biomass, thereby the thermally treated ligno-cellulosic biomass, either before and after fiber shives reduction, may be characterized by having a percent ratio of the amount of xylans to the amount of glucans which is greater than 5%, more preferably greater than 10%, even more preferably greater than 15%, even more preferably greater than 20%, even yet more preferably greater than 25%, and most preferably greater than 30%. On the other hand, less xylans and glucans degradation products, such as furfural and HMF, will be generated in the thermal treatment.

Feedstock Selection

Because the feedstock may use naturally occurring ligno-cellulosic biomass, the stream will have relatively young carbon materials. The following, taken from ASTM D 6866-04 describes the contemporary carbon, which is that found in bio-based hydrocarbons, as opposed to hydrocarbons derived from oil wells, which was derived from biomass thousands of years ago. "[A] direct indication of the relative contribution of fossil carbon and living biospheric carbon can be as expressed as the fraction (or percentage) of contemporary carbon, symbol $f_C$. This is derived from $f_M$ through the use of the observed input function for atmospheric $^{14}C$ over recent decades, representing the combined effects of fossil dilution of the $^{14}C$ (minor) and nuclear testing enhancement (major). The relation between $f_C$ and $f_M$ is necessarily a function of time. By 1985, when the particulate sampling discussed in the cited reference [of ASTM D 6866-04, the teachings of which are incorporated by reference in their entirety] the $f_M$ ratio had decreased to ca. 1.2."

Fossil carbon is carbon that contains essentially no radiocarbon because its age is very much greater than the 5730 year half life of $^{14}C$. Modern carbon is explicitly 0.95 times the specific activity of SRM 4990b (the original oxalic acid radiocarbon standard), normalized to $\delta^{13}C=-19\%$. Functionally, the faction of modern carbon=(1/0.95) where the unit 1 is defined as the concentration of $^{14}C$ contemporaneous with 1950 [A.D.] wood (that is, pre-atmospheric nuclear testing) and 0.95 are used to correct for the post 1950 [A.D.] bomb $^{14}C$ injection into the atmosphere. As described in the analysis and interpretation section of the test method, a 100% $^{14}C$ indicates an entirely modern carbon source, such as the products derived from this process. Therefore, the percent $^{14}C$ of the product stream from the process will be at least 75%, with 85% more preferred, 95% even preferred and at least 99% even more preferred and at least 100% the most preferred. (The test method notes that the percent $^{14}C$ can be slightly greater than 100% for the reasons set forth in the method). These percentages can also be equated to the amount of contemporary carbon as well.

Therefore the amount of contemporary carbon relative to the total amount of carbon is preferred to be at least 75%, with 85% more preferred, 95% even more preferred and at least 99% even more preferred and at least 100% the most preferred. Correspondingly, each carbon containing compound in the reactor, which includes a plurality of carbon containing conversion products will have an amount of contemporary carbon relative to total amount of carbon is preferred to be at least 75%, with 85% more preferred, 95% even preferred and at least 99% even more preferred and at least 100% the most preferred.

In general, a natural or naturally occurring ligno-cellulosic biomass can be one feed stock for this process. Ligno-cellulosic materials can be described as follows:

Apart from starch, the three major constituents in plant biomass are cellulose, hemicellulose and lignin, which are commonly referred to by the generic term lignocellulose. Polysaccharide-containing biomasses as a generic term include both starch and ligno-cellulosic biomasses. Therefore, some types of feedstocks can be plant biomass, polysaccharide containing biomass, and ligno-cellulosic biomass.

Polysaccharide-containing biomasses according to the present invention include any material containing polymeric sugars e.g. in the form of starch as well as refined starch, cellulose and hemicellulose.

Relevant types of naturally occurring biomasses for deriving the claimed invention may include biomasses derived from agricultural crops selected from the group consisting of starch containing grains, refined starch; corn stover, bagasse, straw e.g. from rice, wheat, rye, oat, barley, rape, sorghum; softwood e.g. *Pinus sylvestris, Pinus radiate*; hardwood e.g. *Salix* spp. *Eucalyptus* spp.; tubers e.g. beet, potato; cereals from e.g. rice, wheat, rye, oat, barley, rape, sorghum and corn; waste paper, fiber fractions from biogas processing, manure, residues from oil palm processing, municipal solid waste or the like. Although the experiments are limited to a few examples of the enumerated list above, the invention is believed applicable to all because the characterization is primarily to the unique characteristics of the lignin and surface area.

The ligno-cellulosic biomass feedstock used to derive the composition is preferably from the family usually called grasses. The proper name is the family known as Poaceae or Gramineae in the Class Liliopsida (the monocots) of the flowering plants. Plants of this family are usually called grasses, or, to distinguish them from other graminoids, true grasses. Bamboo is also included. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass leaves are usually alternate, distichous (in one plane) or rarely spiral, and parallel-veined. Each leaf is differentiated into a lower sheath which hugs the stem for a distance and a blade with margins usually entire. The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchard grass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indian grass, bennuda grass and switch grass.

One classification of the grass family recognizes twelve subfamilies: These are 1) anomochlooideae, a small lineage of broad-leaved grasses that includes two genera (Anomochloa, Streptochaeta); 2) Pharoideae, a small lineage of grasses that includes three genera, including Pharus and Leptaspis; 3) Puelioideae a small lineage that includes the African genus Puelia; 4) Pooideae which includes wheat, barley, oats, brome-grass (Bronnus) and reed-grasses (*Calamagrostis*); 5) Bambusoideae which includes bamboo; 6) Ehrhartoideae, which includes rice, and wild rice; 7) Arundinoideae, which includes the giant reed and common reed; 8) Centothecoideae, a small subfamily of 11 genera that is sometimes included in Panicoideae; 9) Chloridoideae including the lovegrasses (*Eragrostis*, ca. 350 species, including teff), dropseeds (*Sporobolus*, some 160 species), finger millet (*Eleusine coracana* (L.) Gaertn.), and the muhly grasses (Muhlenbergia, ca. 175 species); 10) Panicoideae including panic grass, maize, sorghum, sugar cane, most millets, fonio and bluestem grasses; 11) Micrairoideae and 12) Danthoniodieae including pampas grass; with *Poa* which is a genus of about 500 species of grasses, native to the temperate regions of both hemispheres.

Agricultural grasses grown for their edible seeds are called cereals. Three common cereals are rice, wheat and maize (corn). Of all crops, 70% are grasses.

Sugarcane is the major source of sugar production. Grasses are used for construction. Scaffolding made from bamboo is able to withstand typhoon force winds that would break steel scaffolding. Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

Another naturally occurring ligno-cellulosic biomass feedstock may be woody plants or woods. A woody plant is a plant that uses wood as its structural tissue. These are typically perennial plants whose stems and larger roots are reinforced with wood produced adjacent to the vascular tissues. The main stem, larger branches, and roots of these plants are usually covered by a layer of thickened bark. Woody plants are usually either trees, shrubs, or lianas. Wood is a structural cellular adaptation that allows woody plants to grow from above ground stems year after year, thus making some woody plants the largest and tallest plants.

These plants need a vascular system to move water and nutrients from the roots to the leaves (xylem) and to move sugars from the leaves to the rest of the plant (phloem). There are two kinds of xylem: primary that is formed during primary growth from procambium and secondary xylem that is formed during secondary growth from vascular cambium. What is usually called "wood" is the secondary xylem of such plants.

The two main groups in which secondary xylem can be found are:
1) conifers (Coniferae): there are some six hundred species of conifers. All species have secondary xylem, which is relatively uniform in structure throughout this group. Many conifers become tall trees: the secondary xylem of such trees is marketed as softwood.
2) angiosperms (Angiospermae): there are some quarter of a million to four hundred thousand species of angiosperms. Within this group secondary xylem has not been found in the monocots (e.g. Poaceae). Many non-monocot angiosperms become trees, and the secondary xylem of these is marketed as hardwood.

The term softwood useful in this process is used to describe wood from trees that belong to gymnosperms. The gymnosperms are plants with naked seeds not enclosed in an ovary. These seed "fruits" are considered more primitive than hardwoods. Softwood trees are usually evergreen, bear cones, and have needles or scale like leaves. They include conifer species e.g. pine, spruces, firs, and cedars. Wood hardness varies among the conifer species.

The term hardwood useful for this process is used to describe wood from trees that belong to the angiosperm family. Angiosperms are plants with ovules enclosed for protection in an ovary. When fertilized, these ovules develop into seeds. The hardwood trees are usually broad-leaved; in temperate and boreal latitudes they are mostly deciduous, but in tropics and subtropics mostly evergreen. These leaves can be either simple (single blades) or they can be compound with leaflets attached to a leaf stem. Although variable in shape all hardwood leaves have a distinct network of fine veins. The hardwood plants include e.g. Aspen, Birch, Cherry, Maple, Oak and Teak.

Therefore a preferred naturally occurring ligno-cellulosic biomass may be selected from the group consisting of the grasses and woods. Another preferred naturally occurring ligno-cellulosic biomass can be selected from the group consisting of the plants belonging to the conifers, angiosperms, Poaceae and families. Another preferred naturally occurring ligno-cellulosic biomass may be that biomass having at least 10% by weight of it dry matter as cellulose, or more preferably at least 5% by weight of its dry matter as cellulose.

The carbohydrate(s) comprising the invention is selected from the group of carbohydrates based upon the glucose, xylose, and mannose monomers and mixtures thereof.

The feedstock comprising lignin can be naturally occurring ligno-cellulosic biomass that has been ground to small particles, or one which has been further processed. One process for creating the feedstock comprising lignin, comprises the following steps.

Preferable Pretreatment

It has been theorized that pretreatment of the feedstock is a solution to the challenge of processing an insoluble solid feedstock comprising lignin or polysaccharides in a pressurized environment. According to US 2011/0312051, sizing, grinding, drying, hot catalytic treatment and combinations thereof are suitable pretreatment of the feedstock to facilitate the continuous transporting of the feedstock. While not presenting any experimental evidence, US 2011/0312051 claims that mild acid hydrolysis of polysaccharides, catalytic hydrogenation of polysaccharides, or enzymatic hydrolysis of polysaccharides are all suitable to create a transportable feedstock. US 2011/0312051 also claims that hot water treatment, steam treatment, thermal treatment, chemical treatment, biological treatment, or catalytic treatment may result in lower molecular weight polysaccharides and depolymerized lignins that are more easily transported as compared to the untreated ones. While this may help transport, there is no disclosure or solution to how to pressurize the solid/liquid slurry resulting from the pre-treatment. In fact, as the inventors have learned the conventional wisdom and conventional systems used for pressuring slurries failed when pre-treated ligno-cellulosic biomass feedstock is used.

In the integrated second generation industrial operations, pre-treatment is often used to ensure that the structure of the ligno-cellulosic content is rendered more accessible to the catalysts, such as enzymes, and at the same time the concentrations of harmful inhibitory by-products such as acetic acid, furfural and hydroxymethyl furfural remain substantially low. There are several strategies to achieve increased accessibility, many of which may yet be invented.

The current pre-treatment strategies imply subjecting the ligno-cellulosic biomass material to temperatures between 110-250° C. for 1-60 min e.g.:
  Hot water extraction
  Multistage dilute acid hydrolysis, which removes dissolved material before inhibitory substances are formed
  Dilute acid hydrolyses at relatively low severity conditions
  Alkaline wet oxidation
  Steam explosion.

A preferred pretreatment of a naturally occurring ligno-cellulosic biomass includes a soaking of the naturally occurring ligno-cellulosic biomass feedstock and a steam explosion of at least a part of the soaked naturally occurring ligno-cellulosic biomass feedstock.

The soaking occurs in a substance such as water in either vapor form, steam, or liquid form or liquid and steam together, to produce a product. The product is a soaked biomass containing a first liquid, with the first liquid usually being water in its liquid or vapor form or some mixture.

This soaking can be done by any number of techniques that expose a substance to water, which could be steam or liquid or mixture of steam and water, or, more in general, to water at high temperature and high pressure. The temperature should be in one of the following ranges: 145 to 165° C., 120 to 210° C., 140 to 210° C., 150 to 200° C., 155 to 185° C., 160 to 180° C. Although the time could be lengthy, such as up to but less than 24 hours, or less than 16 hours, or less than 12 hours, or less than 9 hours, or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

If steam is used, it is preferably saturated, but could be superheated. The soaking step can be batch or continuous, with or without stirring. A low temperature soak prior to the high temperature soak can be used. The temperature of the low temperature soak is in the range of 25 to 90° C. Although the time could be lengthy, such as up to but less than 24 hours, or less than 16 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

Either soaking step could also include the addition of other compounds, e.g. $H_2SO4$, $NH_3$, in order to achieve higher performance later on in the process. However, it is preferred that acid, base or halogens not be used anywhere in the process or pre-treatment. The feedstock is preferably void of added sulfur, halogens, or nitrogen. The amount of sulfur, if present, in the composition is in the range of 0 to 1% by dry weight of the total composition. Additionally, the amount of total halogens, if present, are in the range of 0 to 1% by dry weight of the total composition. By keeping halogens from the feedstock, there are no halogens in the lignin conversion products.

The product comprising the first liquid is then passed to a separation step where the first liquid is separated from the soaked biomass. The liquid will not completely separate so that at least a portion of the liquid is separated, with preferably as much liquid as possible, in an economic time frame. The liquid from this separation step is known as the first liquid stream comprising the first liquid. The first liquid will be the liquid used in the soaking, generally water and the soluble species of the feedstock. These water soluble species are glucan, xylan, galactan, arabinan, glucolygomers, xyloolygomers, galactolygomers and arabinolygomers. The solid biomass is called the first solid stream as it contains most; if not all, of the solids. The separation of the liquid can again be done by known techniques and likely some which have yet to be invented. A preferred piece of equipment is a press, as a press will generate a liquid under high pressure.

The first solid stream is then steam exploded to create a steam exploded stream, comprising solids and a second liquid. Steam explosion is a well known technique in the biomass field and any of the systems available today and in the future are believed suitable for this step. The severity of the steam explosion is known in the literature as Ro, and is a function of time and temperature and is expressed as in the Experimental Section.

EXPERIMENTAL

Preparation of Thermally Treated Ligno-Cellulosic Biomass

Wheat straw was used as the ligno-cellulosic biomass feedstock.

Wheat straw was subjected to a thermal treatment composed of a soaking step followed by a steam explosion step according to the following procedure.

Ligno-cellulosic biomass was introduced into a continuous reactor and subjected to a soaking treatment. The soaked mixture was separated into a soaked liquid and a fraction containing the solid soaked raw material by means of a press. The fraction containing the solid soaked raw material was subjected to steam explosion. Steam exploded products were separated into a steam explosion liquid and a steam exploded solid. Steam exploded solid is the exemplary thermally treated ligno-cellulosic biomass before fiber shives reduction used in the present experimental section and they are indicated by the -BSR (Before fiber Shives Reduction) extension following the sample code.

Pretreatment parameters of the ligno-cellulosic biomass are reported in Table 1.

Severity of each thermal treatment step $R_{01}$ and $R_{02}$ was calculated according the formula:

$$R_{01} = \log_{10}(Q_1), \text{ wherein}$$

$$Q_1 = t_1 \exp((T_1 - 100)/14.75)$$

$$R_{02} = \log_{10}(Q_2), \text{ wherein}$$

$$Q_2 = t_2 \exp((T_2 - 100)/14.75),$$

wherein time $t_1$ and $t_2$ is measured in minutes and temperature $T_1$ and $T_2$ is measured in Celsius.

The total severity factor $R_0$ was calculated according to the formula:

$$R_0 = \log_{10}(Q_1 + Q_2)$$

TABLE 1

Process parameters used in the thermal treatment

| | Soaking | | Steam explosion | | | | |
|---|---|---|---|---|---|---|---|
| Sample | Temperature (° C.) | Time (minutes) | Temperature (° C.) | Time (minutes) | $R_{01}$ | $R_{02}$ | $R_0$ |
| S01-BSR | 155 | 65 | 180 | 2 | 3.43 | 2.66 | 3.50 |
| S02-BSR | 155 | 65 | 195 | 2 | 3.43 | 3.10 | 3.60 |
| S03-BSR | 155 | 65 | 187 | 8 | 3.43 | 3.46 | 3.75 |
| S04-BSR | 155 | 65 | 195 | 4 | 3.43 | 3.40 | 3.72 |
| S05-BSR | 155 | 65 | 202 | 8 | 3.43 | 3.91 | 4.03 |
| S06-BSR | 155 | 65 | 210 | 16 | 3.43 | 4.44 | 4.48 |
| S07-BSR | 158 | 65 | 201.5 | 4 | 3.52 | 3.59 | 3.86 |
| S08-BSR | 158 | 65 | 202.5 | 2 | 3.52 | 3.32 | 3.73 |

Fiber Shives Reduction of the Thermally Treated Ligno-Cellulosic Biomass

All the thermally treated ligno-cellulosic biomass were subjected to a fiber shives reduction step by means of a counter-rotating twin screw extruder (Welding Engineers Inc., model HTR 30 MM (HTR 30.22.22.22.13.E1), Blue Bell, Pa.), barrel length to screw diameter ratio of 54:1. The machine was fitted to a 25-hp motor, which has a provision to adjust the screw speed from 0 to 500 rpm. The parameters of the profile of the screws are reported in FIG. 6.

The thermally treated ligno-cellulosic biomass was treated at 250 rpm to reduce fiber shives. The thermally treated ligno-cellulosic biomass was inserted in the extruder at a temperature of 25° C. The thermally treated ligno-cellulosic biomass exited the extruder as a solid at about 25° C. The thermally treated ligno-cellulosic biomass was inserted manually in the extruder at an inlet rate of approximately 5 Kg/h on wet basis, at a moisture content of about 60%. Residence time was estimated be to approximately 3 minutes.

The specific energy consumption for fiber shives reducing a Kg of thermally treated ligno-cellulosic biomass was evaluated by the equation:

$$SEC = \text{Absorbed power}/T,$$

wherein Absorbed power is measured in W, T is the material throughput, in Kg/h and SEC is measured in Wh/Kg.

The absorbed power is the electrical power absorbed by the electrical engine of the extruder. Thereby, the SEC parameter is an overestimation of the specific mechanical energy (SME), which is a parameter often reported in the prior art and is the mechanical energy applied to the thermally pretreated ligno-cellulosic biomass (see for example Wen-Hua Chen et al., Bioresource Technology 102 (2011), p. 10451).

The SEC was evaluated to be in the range of 0.1-0.2 kWh/Kg of thermally treated ligno-cellulosic biomass on wet basis. The specific energy consumption is much lower that the specific energy reported in the prior art, as for example in WO2011044292A2, wherein an energy of 1.03 kWh/kg is used.

The extruded thermally treated ligno-cellulosic biomass for reducing fiber shives is the exemplary thermally treated ligno-cellulosic biomass after fiber shives reduction used in the following examples and are indicated by the -ASR (After fiber Shives Reduction) extension following the sample code.

Composition

Composition of materials was determined according to standard analytical methods listed at the end of the experimental section to quantify soluble sugars (glucose, xylose, glucooligomers and xylooligomers), insoluble sugars (glucans and xylans), xylans degradation products (furans, such as furfural), glucans degradation products (HMF), and lignin and other compounds. The compositions of corresponding BSR and ASR materials were identical within the measurement error and only ASR compositions of exemplary samples (S01 to S06) are reported in Table 2. Results are reported in terms of weight percent of the dry matter of the samples. It is noted that the percent amount of glucans and xylans degradation products is negligible or very low, namely less than 1% in all the samples, thanks to the low severity of the thermal treatment. Acetic acid is produced as an effect of the thermal treatment on the acetyl groups in the ligno-cellulosic biomass and it is considered an enzyme inhibitory compound, but not a sugar degradation product which potentially limits the yield of the process. Also the content of acetic acid is negligible. It is noted that the percent ratio of insoluble xylans to insoluble glucans decreases with severity factor $R_{02}$, as the thermal treatment removes preferentially xylans.

TABLE 2

Composition of thermally treated biomass after fiber shives reduction.

| Composition, % wt. DB | S1-ASR | S2-ASR | S3-ASR | S4-ASR | S5-ASR | S6-ASR |
|---|---|---|---|---|---|---|
| Glucose | 0 | 0 | 0 | 0 | 0.101 | 0.088 |
| Xylose | 0 | 0.244 | 0 | 0.8 | 1.734 | 1.546 |
| Glucolygomers | 0 | 0.258 | 0 | 0.556 | 0.77 | 0.731 |
| Xylolygomers | 0 | 3.849 | 0 | 4.886 | 2.112 | 2.634 |
| Insoluble glucans | 43.658 | 46.392 | 50.271 | 47.844 | 42.705 | 44.394 |

TABLE 2-continued

Composition of thermally treated biomass after fiber shives reduction.

| Composition, % wt. DB | S1-ASR | S2-ASR | S3-ASR | S4-ASR | S5-ASR | S6-ASR |
|---|---|---|---|---|---|---|
| Insoluble xylans | 13.498 | 14.637 | 13.046 | 11.122 | 3.994 | 3.79 |
| Lignin | 20.685 | 22.498 | 23.225 | 22.61 | 21.34 | 22.723 |
| Others | 22.159 | 11.933 | 13.458 | 11.945 | 26.656 | 23.351 |
| Furfural | 0 | 0.007 | 0 | 0.024 | 0.057 | 0.08 |
| HMF | 0 | 0.024 | 0 | 0.043 | 0.119 | 0.142 |
| Acetic Acid | 0 | 0.158 | 0 | 0.17 | 0.412 | 0.521 |
| Insoluble xylans/ insoluble glucans | 0.309 | 0.316 | 0.26 | 0.232 | 0.094 | 0.085 |
| Insoluble glucans/ lignin | 2.11 | 2.06 | 2.16 | 2.12 | 2.00 | 1.95 |

Glucose/Xylose Recovery and Glucans Accessibility

Glucose recovery is the percent ratio between the total amount of glucans in the thermally treated biomass before fiber shives reduction (as glucose equivalent calculated including insoluble glucans, gluco-oligomers, cellobiose and glucose present in both solid and liquid streams) and the amount of glucans (converted in glucose equivalent) present in the raw material before the thermally treatment. The complementary to 100% of the glucose recovery represent therefore the total amount of glucans degradation products as an effect of the thermal treatment.

Xylose recovery is the percent ratio between the total amount of xylans in the thermally treated biomass before fiber shives reduction (as xylose equivalent calculated including insoluble xylans, xylo-oligomers, xylobiose and xylose present in both solid and liquid streams) and the amount of xylans (converted in xylose equivalent) present in the raw material before the thermal treatment. The complementary to 100% of the xylose recovery represents therefore the total amount of xylans degradation products as an effect of the thermal treatment.

Glucans accessibility is defined as the percent amount of insoluble glucans enzymatically hydrolyzed to soluble compounds with respect to the amount of insoluble glucans in the pre-treated materials (before and after fiber shives reduction) and calculated as (1−% insoluble glucans at the end of the hydrolysis)/(% insoluble glucans at the beginning of the hydrolysis), when hydrolysis is conducted in excess of enzymes and for a long time. Glucans accessibility was determined according to the following procedure.

Pretreated material was mixed with water in a volume of 1500 ml to obtain a mixture having a 7.5% dry matter content and the mixture was inserted into an enzymatic reactor. pH was set to 5.2 and temperature was set to 50° C. An enzyme cocktail (CTec3 by Novozymes) was added, corresponding to a concentration of 26 g of cocktail solution per 100 gram of glucans contained in the mixture.

Enzymatic hydrolysis was carried out for 48 hours under agitation. The content of glucans, glucose and glucooligomers in the mixture was measured at different times of the enzymatic hydrolysis.

Glucans accessibility and xylose and glucose recovery was determined for all the BSR and ASR materials.

In FIG. 7 the glucans accessibility and in FIG. 8 the xylose and glucose recovery in function of $R_{O2}$ are reported. All the plots in this experimental section are reported in function of $R_{O2}$, as this severity factor is related to the steam explosion effect. Similar considerations hold in the case that $R_O$ is considered as the independent variable in the graphs.

It is noted that glucans accessibility of BSR material increases by increasing severity factor, but a bigger amount of xylans are degraded. The fiber shives reduction treatment is effective to increase the glucans accessibility at low severity factor, without degrading xylans (or degrading a very few amount of) to degradation products. Thereby, also at low severity factor, a glucans accessibility greater than 90% is obtained. Increasing the severity factor, the effectiveness of the fiber shives reduction treatment on glucans accessibility is less pronounced.

In the case of glucans recovery, the degradation effect is less pronounced but the effects of thermal and fiber shives reduction treatment are similar to those observed for xylans recovery.

Automated Optical Analyses

The samples were analyzed by automated optical analysis, using unpolarized light for determining fibres, fines and fiber shives content, as well as length and width. ISO 16065 2:2007 protocol was used in fibres analyses.

The instrument used was a MorFi analyser from Techpap, Grenoble, France.

Briefly, 2 g of air dried sample was disintegrated in a low consistency pulper for 2000 revolutions in approximately 2 liters of tap water, thus reaching a stock concentration of about 1 g/l.

The suspension was stirred very well before withdrawing the sample to perform the measurement according to the manufacturer's instructions. Each sample was run in duplicate or in triplicate in case of higher standard deviation.

According to Morfi analysis software, the treated lignocellulosic biomass is composed by:

Fiber shives: elements having a width greater than 75 micron

Fibres: elements having a width equal to or less than 75 micron and a length greater than 200 micron Fines: having a width equal to or less than 75 micron and a length less than 200 micron The width of the fibres, fines and fibers shives remained substantially unchanged after the fiber shives reduction treatment.

In the graphs of FIG. 9 it is reported the area-weighted distribution of fibres and fines length of BSR and ASR materials produced at low severity factor (S02-BSR and S02-ASR, FIG. 9a) and high severity factor (S05-BSR and S05-ASR, FIG. 9b) relative to all the sample. Briefly, the percent area value of each length class has been calculated as percent ratio of the sum of the area of all the fibres and fines in each length class and the sum of the area of all the fines, fibres, and fiber shives.

It is noted that S05-BSR has a greater percent area of fines and a lower percent area of long fibres with respect to S02-BSR, as expected considering the higher severity of S05-BSR thermal treatment. This corresponds to a higher glucans accessibility of S05-BSR (about 95%) with respect to S02-BSR (84%).

The fiber chive reduction treatment reduces the percent area of long fibres (or equivalently the number of long fibres) and increases the population of fines and short fibres in both the samples, but:

the reduction of the percent area of long fibres in S05-ASR, with respect to S05-BSR, is similar to the corresponding reduction in S02-ASR;

the percent area of fines in S05-ASR is greater than in S02-ASR;

despite the fact that S05-ASR contains more fines/short fibres than S05-BSR (in other words, it is more refined), the accessibility is unchanged within the experimental error (93% and 94%);

despite the fact that S05-ASR contains more fines/short fibres than S02-ASR, the corresponding accessibility are very close (93% and 92% respectively).

In the graph of FIG. 10 it is reported the area-weighted distribution of fiber shives of S02-BSR (FIG. 10a) and S05-BSR (FIG. 10b) and related ASR materials. The percent area value of each length class has been calculated as percent ratio of the sum of the area of all the fiber shives in each length class to the sum of the areas of all the fines, fibres, and fiber shives.

It is highlighted that:

S05-BSR has a lower percent area of shives than S02-BSR, in particular shives longer than about 737 µm, evidencing that that steam explosion is effective in reducing big shives;

the percent area of shives is strongly reduced by the mechanical treatment in S02-BSR, due to the large starting shives population.

the accessibility of S02-BSR is strongly enhanced by the reduction in long shives population;

The accessibility of S05-BSR is not affected by the fiber shives reduction treatment because the limited percent area of long shives.

In the graph of FIG. 11 it is reported the percent area of all the shives having a length greater than 737 µm in function of the second severity cooking $R_{o2}$ for exemplary samples before and after fiber shives reduction. S06-BSR was produced at the maximum severity factor of $R_{o2}$ of 4.44 sufficient to remove substantially all shives. The percent area of all the shives having a length greater than 737 µm has been calculated as the percent ratio of the sum of the areas of all the shives and the sum of the areas of all the fines, fibres, and fiber shives.

These results highlight the fact that the increase in glucans accessibility is not strictly related to fibre size reduction, that is, once the fibres are accessible to the enzyme, any further decrease in fibre length is not effective on enzymatic accessibility of the fibre, thereby energy is spent without obtaining any beneficial effect on accessibility.

Instead, experiments show that it is the reduction of the amount of fiber shives to be effective on the enzymatic accessibility, depending clearly from the starting population of fiber shives. If the thermal treatment is performed at a severity high enough to produce a thermally treated material having a low amount of fiber shives, more specifically of long fiber shives, the fiber shives reduction treatment has not effect on the accessibility of the material. Unfortunately, such a high severity thermal treatment degrade a relevant amount of glucans and xylans to detrimental degradation products.

Basically, the experiments highlight that fiber shives are fiber bundles which are not accessible to the enzymes, thereby limiting the glucans accessibility, and that the fiber shives reduction treatment is useful when it convert fiber shives to fibres. As a consequence, the combination of the thermal treatment in mild conditions and the treatment to reduce the amount of fiber shives increases the glucans accessibility and xylose recovery without degrading a significant amount of sugars in the ligno-cellulosic biomass.

Torque Measurement of Slurried Samples

Torque measurement experiments were run in a cylindrical vessel whose characteristics are here reported.

D (diameter)=105 mm
H (height)=145 mm

The reactor is fitted with a stirrer tool IKA R 1375 to give the following configurations:

D (stirrer width)=70 mm
D (stirrer height)=70 mm
H (stirrer distance from the vessel bottom)=10 mm Agitation was provided by IKA Eurostar 60 control motors (power: 126 W).

With no material inserted, the no load torque at 50 rpm was 0 N cm. An amount of material corresponding to 80 gr on dry basis was inserted in the vessel and water was added to reach a dry matter of 20%.

The mixture was agitated at 50 rpm for 10 seconds. The torque value of each run was calculated as the mean of the maximum and minimum value during 5 seconds measuring time.

The measurement was replicated three times and the torque was calculated as the mean value of the three runs.

After each torque measurement at a fixed dry matter, dry matter was reduced to 18%, 16%, 14%, 12%, 10%, 8% by subsequent addition of water. Temperature was maintained to 25° C.

In table 3 torque values of exemplary samples, collected at different dry matter, are reported. Values below the sensitivity of the measurements are reported as 0.

TABLE 3

| Torque measurements of samples at different dry matter Torque, N * cm | | | | | | | | | | |
|---|---|---|---|---|---|---|---|---|---|---|
| DM, % | S01-BSR | S01-ASR | S02-BSR | S02-ASR | S03-BSR | S03-ASR | S04-BSR | S04-ASR | S05-BSR | S05-ASR |
| 20% | 87 | 11 | 49 | 8 | 59 | 17 | 36 | 2 | 0 | 0 |
| 18% | 54 | 7 | 40 | 6 | 45 | 10 | 20 | 1 | 0 | 0 |
| 16% | 43 | 5 | 31 | 3 | 31 | 8 | 13 | 0 | 0 | 0 |
| 14% | 25 | 5 | 19 | 2 | 17 | 5 | 8 | 0 | 0 | 0 |
| 12% | 17 | 3 | 10 | 1 | 11 | 3 | 5 | 0 | 0 | 0 |
| 10% | 9 | 1 | 6 | 0 | 8 | 1 | 1 | 0 | 0 | 0 |
| 8% | 3 | 0 | 1 | 0 | 3 | 0 | 0 | 0 | 0 | 0 |

In FIG. 12 the torque of S01 and S04 samples (BSR and corresponding ASR materials), measured at different dry matter, are plotted as an example.

In FIG. 13 the torque measured at 18% dry matter as a function of the severity factor is reported.

It is noted that at fixed dry matter the torque values decreases by increasing the thermal treatment severity factor and that samples thermally treated at the highest severity factor present a torque value which is very small—or zero—even at the high dry matter values. Torque values are dependent from the experimental setup and procedure used, but they are directly related to viscosity measurements. Thereby, viscosity strongly decrease increasing the severity factor of the thermal treatment.

By applying the disclosed fiber shives reduction treatment to the thermally treated samples, the torque values at each dry matter decrease and this effect is enhanced at low severity. Thereby, the combination of the thermal treatment in mild conditions and the treatment to reduce the amount of fibers shives of the thermally treated biomass strongly reduces the torque/viscosity of a slurry of the corresponding thermally treated biomass after fiber shives reduction. Again, this is obtained without degrading significant amount of sugars of the ligno-cellulosic biomass.

As reported in following experimental sections, the torque/viscosity values of the slurry prepared using the thermally treated ligno-cellulosic biomass after shives reduction are comparable to the torque/viscosity values of corresponding thermally treated biomass before fiber shives reduction which have been enzymatically hydrolyzed.

Saturation Humidity

Saturation humidity is the maximum amount of water that could be absorbed by the ligno-cellulosic biomass. The water added to the material after the material has reached its saturation humidity value is not entrapped into the solid material and will be present as free water outside the solid. Material properties evaluated using the saturation humidity procedure are equivalent to those given by the well-known in the art Water Retention Value (WRV) procedure. Saturation humidity procedure is easier and could be performed without dedicated equipment with respect to WRV.

Saturation humidity is correlated to torque/viscosity of the slurried ligno-cellulosic biomass, but it is related to not-slurried ligno-cellulosic biomass.

Saturation humidity was measured according to the following methodology:

An amount of 20 gr of sample on dry matter basis was inserted in a becker and water (up to 50 ml) was added in 2 ml aliquots every 1 h and hand shaken to allow the material adsorb the water. The procedure ends when water added is not absorbed into the material after the 1 h incubation and water drops are observed on the surface of the material. Measurements were performed at 25° C. The saturation humidity is calculated as the total amount of water absorbed into the material (initial moisture content plus the amount of water added), divided by the weight of the material on a dry basis.

The saturation humidity of samples prepared at different severity factor $R_{02}$ before and after fiber shives reduction is reported in FIG. 14. One of the effects of the disclosed fiber shives reduction treatment is to reduce the saturation humidity, and this result is also correlated to the decrease of torque/viscosity observed for ASR slurries with respect to BSR slurry. It is noted that in the prior art an increase of WRV (which is equivalent to saturation humidity) is usually related to micro-fibrillation of fibres, that is a mechanical treatment used to open up the fibres that consequently adsorb more water (see I. C. Hoeger et al., Cellulose (2013)20:807-818).

A similar concept is expressed in S. H. Lee et al., Bioresource Technology, 2010, 101, p. 9645-9649, and in S. H. Lee et al., Bioresource Technology, 2010, 101, p. 769-774, where a thermally treated biomass is subjected to a mechanical treatment by means on an extruder operated in condition to fibrillate the feedstock into submicron and/or nanoscale fibres, even if no WRV/saturation humidity measurements are presented.

Thereby, according to the prior art consideration, the fiber shives reduction treatment presently disclosed does not fibrillate the fibres.

Comparison of Torque of Slurried Thermally Treated Biomass after Fiber Shives Reduction and Thermally Treated Biomass Before Fiber Shives Reduction During Enzymatic Hydrolysis To better demonstrate the importance of forming a low viscosity slurry from the thermally treated biomass after shives reduction without any added enzymes, a further sample was prepared, at the following conditions:

| Sample | Soaking | | Steam explosion | | $R_{01}$ | $R_{02}$ | $R_0$ |
| | Temperature (° C.) | Time (minutes) | Temperature (° C.) | Time (minutes) | | | |
| --- | --- | --- | --- | --- | --- | --- | --- |
| S09-BSR | 155 | 65 | 190 | 4 | 3.43 | 3.25 | 3.65 |

Fiber shives reduction step was performed by means of the extruder according to the process previously described.

Torque measurement experiments were run in two identical anchor impeller, herein referred to reactor A and reactor B, whose characteristics are here reported.

T (reactor diameter)=0.15 m-Z (reactor height)=0.30 m
jacket for heat exchange fluid all around the lateral surface and bottom, with a width of 4 cm;
hemi-spherical bottom;
cover with gasket and seal, with 5 openings (1 center hole for stirrer shaft; 4 side holes to 30 add materials or for sampling, that during the tests will be closed with caps).

The two reactors are fitted with two identical anchor agitators to give the following configurations:

D ("wingspan")=0.136 m
S (blade width)=0.019 m
H (anchor height)=0.146 m
5 C (clearance, blade-wall distance)=0.007 m Agitation was provided by Heidolph RZR 2102 control motors (power: 140 W).

With no material inserted, the no load torque at 23 rpm was 23 N cm. An amount of 800 gr of BSR material having a moisture content of 60% was inserted in reactor A and soaking liquid was added at a ratio of 1:0.67. The dry matter was progressively adjusted to reach a final dry matter of 15% by addition of water at the end of the experiment.

An amount of 800 gr of ASR material having a dry matter content of 40% was inserted in reactor B and soaking liquid was added at a ratio of 1:0.67. The dry matter was progressively adjusted to reach a final dry matter of 15% by addition of water at the end of the experiment.

Temperature in both reactors was 25° C.

The two mixtures were agitated at 23 rpm for 90 minutes with no enzymes added.

Viscosity reduction was then conducted in both reactors, at a temperature of 50° C.

pH was corrected to 5 by means of a KOH solution. Viscosity reduction was conducted by inserting Ctec3 enzymatic cocktail by Novozymes at a concentration of 4.5 gr of enzyme cocktail every 100 g gram of glucans contained in the BSR and ASR solid materials. Viscosity reduction was conducted for 48 hours under agitation.

Torque was recorded for all the experiment time. No load torque was subtracted by the measured torque. The torque of the mixture comprising the material before fiber shives reduction without enzymes was approximately constant at a value close to 110 N cm till the insertion of enzymes. Then torque value was found to decrease after enzyme addition as usually occurs during hydrolysis. The torque of the mixture comprising the material after fiber shives reduction was found to be very low and close to the torque value of the hydrolyzed stream even before enzymes addition.

Figure 15:
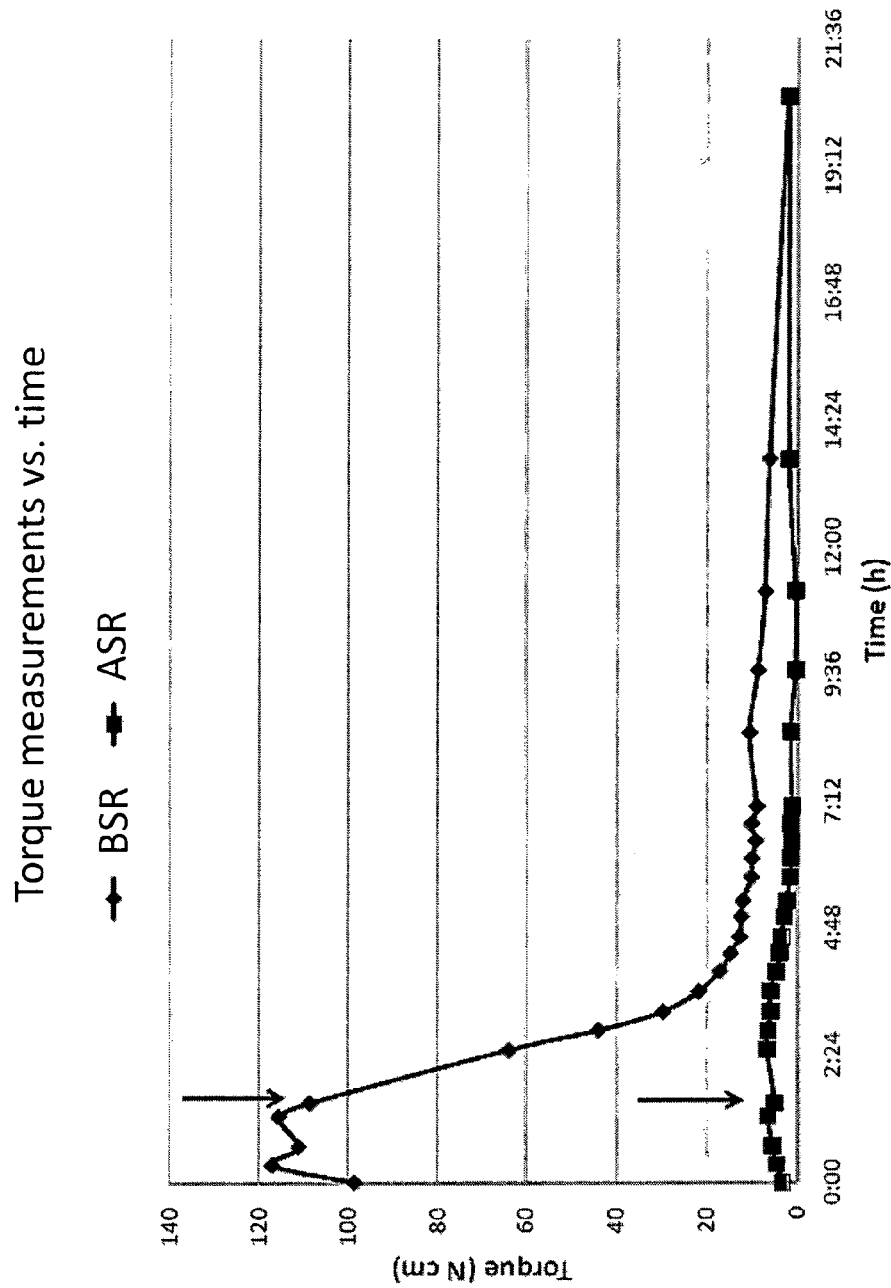
FIG. 15 plots the torque measurement versus time of thermally treated ligno-cellulosic biomass before and after fiber shives reduction.

FIG. 15 reports torque values of the two slurries during the first 21 hours of mixing time. Torque values remained approximately constant after this period and for the remaining mixing time in both reactors. Time zero corresponds to the start of agitation. Arrows indicate enzymes addition in both reactors.

Rheological and Viscosity Measurements

Different amounts of BSR and ASR of the sample having $R_{02}=3.25$ were added to water to prepare 600 ml slurry samples at different dry matter content on dry basis, ranging from 5 to 17%. The samples were agitated up to 15 minutes until reaching a visually well dispersed slurries.

Rheological measurements were performed using a RheolabQC at 25° C. Data were collected corresponding to a shear rate ranging from 0.01 to 100 s$^{-1}$ and at a slope of 6 Pt./dec. Table 4 reports the measured shear stress and viscosity values for ASR slurries having a dry matter of 5%, 7%, 9%, 11%. The viscosity is not constant and decreases with the increase of shear rate. It was not possible to measure BSR slurries on RheolabQC at 25° C. even at a dry matter lower than 5% due to the high viscosity of the sample. This is a remarkable difference in the rheological properties of BSR and ASR slurries.

TABLE 4

Rheological parameters of ASR slurries having a dry matter content of 5%, 7%, 9%, 11%.

| Shear Rate, | Shear Stress, Pa | | | | Viscosity, Pa · s | | | |
|---|---|---|---|---|---|---|---|---|
| | Dry matter | | | | | | | |
| 1/s | 5% | 7% | 9% | 11% | 5% | 7% | 9% | 11% |
| 0.10 | 0.72 | 0.69 | 1.11 | 18.10 | 7.2 | 6.90 | 11.1 | 181 |
| 0.15 | 0.68 | 0.82 | 0.71 | 20.30 | 4.66 | 5.60 | 4.84 | 138 |
| 0.22 | 0.63 | 1.26 | 0.62 | 23.60 | 2.9 | 5.87 | 2.9 | 110 |
| 0.32 | 0.62 | 1.84 | 0.94 | 27.70 | 1.97 | 5.82 | 2.97 | 87.7 |
| 0.46 | 1.14 | 1.63 | 1.33 | 35.10 | 2.47 | 3.50 | 2.87 | 75.7 |
| 0.68 | 0.96 | 1.53 | 0.64 | 47.70 | 1.41 | 2.25 | 0.932 | 70.1 |
| 1.00 | 1.17 | 1.16 | 1.19 | 58.10 | 1.17 | 1.16 | 1.19 | 58.2 |
| 1.47 | 0.81 | 0.67 | 1.01 | 43.20 | 0.553 | 0.45 | 0.687 | 29.3 |
| 2.15 | 0.67 | 1.00 | 1.35 | 10.70 | 0.31 | 0.47 | 0.627 | 4.94 |
| 3.16 | 1.36 | 1.77 | 1.00 | 27.10 | 0.429 | 0.56 | 0.317 | 8.61 |
| 4.64 | 0.54 | 1.11 | 1.78 | 18.50 | 0.117 | 0.24 | 0.383 | 3.97 |
| 6.81 | 0.77 | 1.33 | 1.96 | 36.60 | 0.113 | 0.20 | 0.288 | 5.36 |
| 10.00 | 0.74 | 1.56 | 3.23 | 25.30 | 0.074 | 0.16 | 0.323 | 2.53 |
| 14.70 | 1.09 | 1.64 | 4.35 | 28.20 | 0.074 | 0.11 | 0.296 | 1.92 |
| 21.50 | 1.16 | 1.89 | 5.61 | 26.20 | 0.053 | 0.09 | 0.26 | 1.21 |
| 31.60 | 1.61 | 2.05 | 5.05 | 22.40 | 0.050 | 0.06 | 0.16 | 0.70 |
| 46.40 | 0.73 | 2.75 | 4.63 | 24.90 | 0.015 | 0.06 | 0.099 | 0.53 |
| 68.10 | 0.37 | 2.45 | 5.84 | 24.30 | 0.005 | 0.04 | 0.085 | 0.35 |
| 100.00 | 0.44 | 2.62 | 4.36 | 21.60 | 0.004 | 0.03 | 0.043 | 0.21 |

Figure 16:
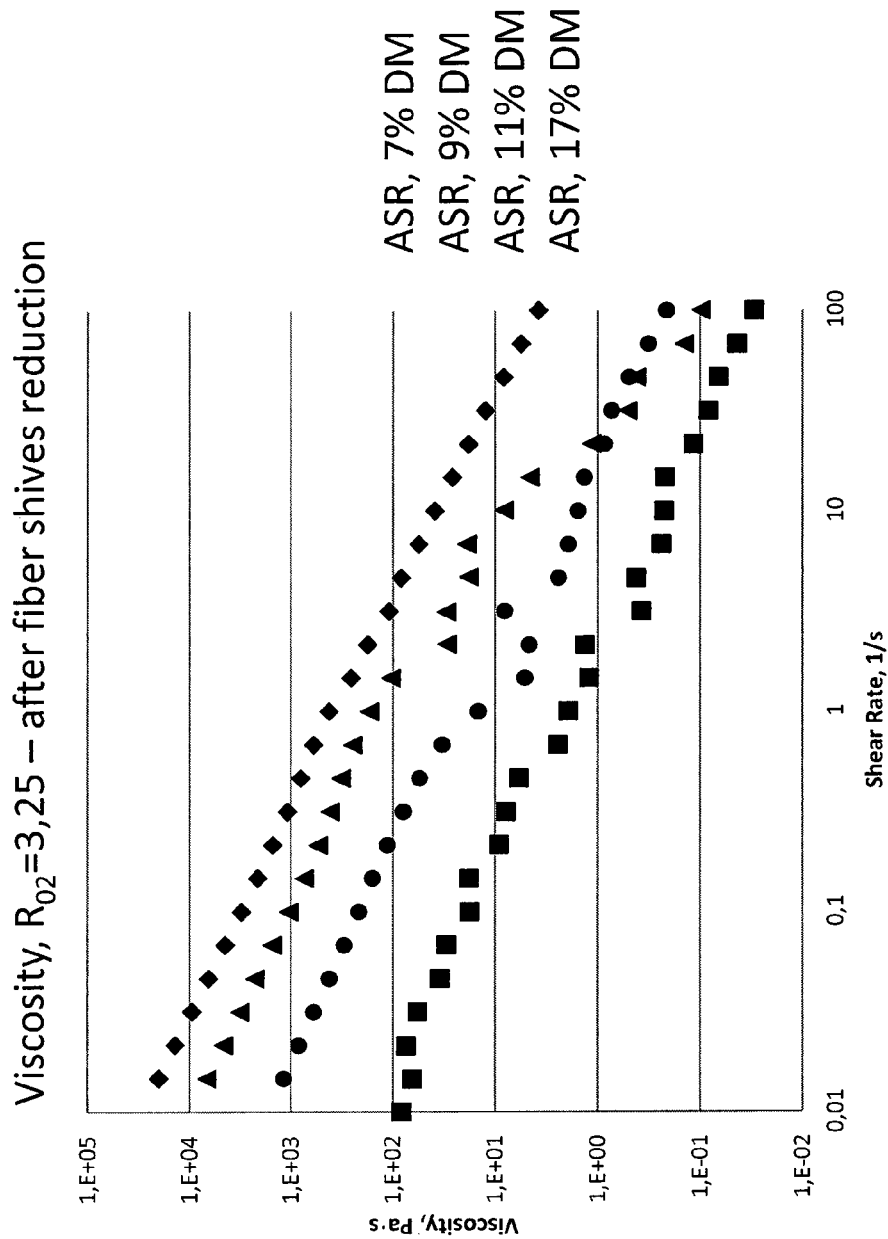
FIG. 16 plots the viscosity of slurries of the thermally treated biomass after fiber shives reduction at different amounts in water.

The viscosity of ASR slurries at 7%, 9%, 11% and 17% are reported in the graph of FIG. 16 on a bi-logarithmic scale. The vertical line in the graph indicates the shear rate value which was selected as the reference value for measuring the viscosity. In the context of the present disclosure, the described RheolabQC instrument procedure for viscosity measurement is the reference method for measuring the viscosity of a slurry.

Figure 17:
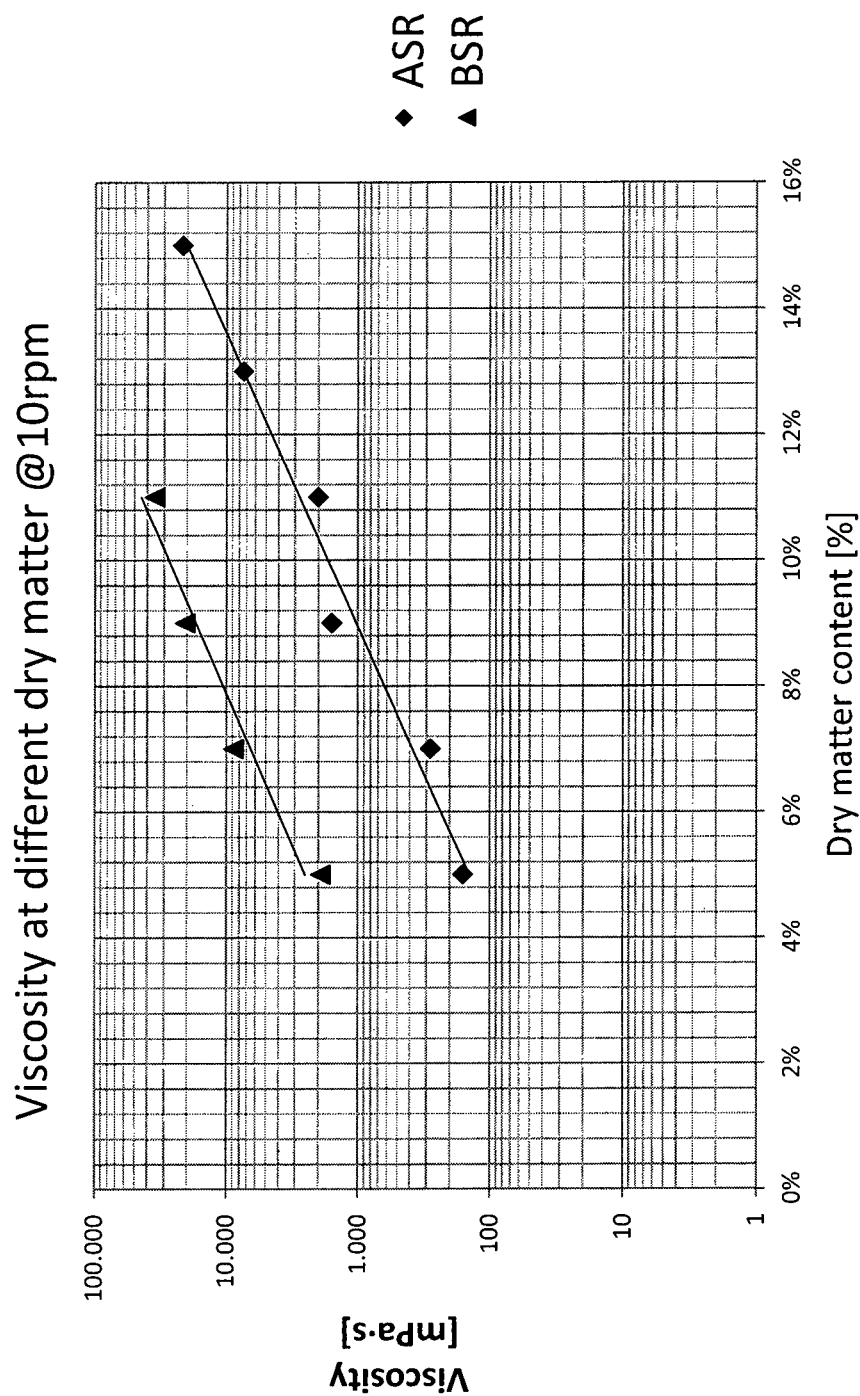
FIG. 17 plots the viscosity of slurries of thermally treated ligno-cellulosic biomass before and after fiber shives reduction at different dry matter contents of the slurry.

Viscosity measurements were performed on BSR and ASR slurry samples also using a Brookfield RVDV-I Prime viscometer following the procedures reported by the producer. All the measurements were performed at 25° C. using a disc spindle #5 on a 600 ml sample. Data were collected starting from 1 rpm and increasing the rotation speed to 2.5, 5, 10, 20, 50 and 100 rpm. In FIG. 17 viscosities of BSR and ASR slurries collected at 10 rpm as a function of dry matter are shown. The graph highlights that the viscosity of the slurry prepared using ASR is about 90% less than that prepared using BSR.

Hydrolysis without Enzymes or Acid Catalysts

Experiments of hydrolysis without enzymes or acid catalysts were conducted on sample S09, prepared at a R02 of 3.25.

A portion of S09-BSR was washed in water to create a washed thermally treated solid ligno-cellulosic biomass, indicated by S09-W-BSR.

Water at 20° C. was added to the thermally treated solid ligno-cellulosic biomass in ratio 10:1 so to eliminate soluble components and water was removed after 15 minutes. Washing procedure was repeated 2 times. At the end, the thermally treated solid ligno-cellulosic biomass was filtered by means of a Buchner filter.

A portion of the thermally treated solid ligno-cellulosic biomass S09-BSR and a portion of the washed thermally treated solid ligno-cellulosic biomass S09-W-BSR were separately subjected to a fiber shives reduction step by means of the counter-rotating twin screw extruder as previously described. The corresponding samples after fiber shives reduction are labeled as S09-ASR and S09-W-ASR respectively.

The solid samples S09-BSR, S09-W-BSR, S09-ASR and S09-W-ASR were used in hydrolysis experiments.

In Table 5 the composition of the liquid biomass solution (LBS) is reported, while in Table 6 the compositions of the solid samples are reported.

TABLE 5

Composition of the liquid biomass solution and acidic stream.

| Composition | | Liquid Biomass stream | Acidic Stream |
|---|---|---|---|
| Dry matter | (%, w/w) | 10.794% | 8.648% |
| xylobiose | (%, w/w) | 0.066% | 0.066% |
| glucose | (%, w/w) | 0.059% | 0.059% |
| xylose | (%, w/w) | 0.300% | 0.302% |
| arabinose | (%, w/w) | 0.197% | 0.198% |
| formic acid | (%, w/w) | 0.243% | 0.245% |
| acetic acid | (%, w/w) | 0.375% | 0.377% |
| levulinic acid | (%, w/w) | 0.000% | 0.000% |
| 5-HMF | (%, w/w) | 0.011% | 0.011% |
| furfural | (%, w/w) | 0.005% | 0.005% |
| Monovalent cation | (%, w/w) | 0.944% | 0.321% |
| Bivalent cation | (%, w/w) | 0.140% | 0.000% |
| glucoligomers | (%, w/w) | 0.412% | 0.415% |
| xyloligomers | (%, w/w) | 2.757% | 2.776% |
| arabinan | (%, w/w) | 0.182% | 0.183% |
| acetyls | (%, w/w) | 0.463% | 0.466% |
| other | (%, w/w) | 4.640% | 3.225% |
| [H$^+$] before acidification treatment | (g-mol H$^+$/L) | 0.00009 | — |
| [H$^+$] after acidification treatment | (g-mol H$^+$/L) | — | 0.10715 |
| pH | | 4.04 | 0.97 |

TABLE 6 compositions of the solid streams used in hydrolysis experiments.

| Composition | | S09-BSR | S09-W-BSR | S09-ASR | S09-W-ASR |
|---|---|---|---|---|---|
| glucose | (%, w/w DB) | 0.00% | 0.00% | 0.00% | 0.00% |
| xylose | (%, w/w DB) | 0.98% | 0.00% | 0.90% | 0.00% |
| arabinose | (%, w/w DB) | 0.17% | 0.00% | 0.00% | 0.00% |
| formic acid | (%, w/w DB) | 0.00% | 0.00% | 0.00% | 0.00% |
| acetic acid | (%, w/w DB) | 0.23% | 0.00% | 0.22% | 0.00% |
| levulinic acid | (%, w/w DB) | 0.00% | 0.00% | 0.00% | 0.00% |
| 5-HMF | (%, w/w DB) | 0.06% | 0.00% | 0.05% | 0.00% |
| furfural | (%, w/w DB) | 0.03% | 0.00% | 0.02% | 0.00% |
| glucoligomers | (%, w/w DB) | 0.67% | 0.00% | 0.63% | 0.00% |
| xyloligomers | (%, w/w DB) | 4.80% | 0.00% | 4.32% | 0.00% |
| arabinan | (%, w/w DB) | 0.12% | 0.00% | 0.26% | 0.00% |
| acetyls | (%, w/w DB) | 0.28% | 0.00% | 0.25% | 0.00% |
| other | (%, w/w DB) | 7.43% | 0.00% | 6.63% | 0.00% |
| insoluble glucans | (%, w/w DB) | 42.40% | 49.74% | 41.48% | 47.84% |
| insoluble xylans | (%, w/w DB) | 7.99% | 9.38% | 8.17% | 9.42% |
| insoluble arabinan | (%, w/w DB) | 0.00% | 0.00% | 0.00% | 0.00% |
| insoluble acetyls | (%, w/w DB) | 0.00% | 0.00% | 0.00% | 0.00% |
| Klason lignin | (%, w/w DB) | 23.22% | 27.24% | 0.00% | 0.00% |
| ashes | (%, w/w DB) | 0.00% | 0.00% | 0.00% | 0.00% |
| insoluble nitrogen | (%, w/w DB) | 0.00% | 0.00% | 0.00% | 0.00% |
| other insoluble | (%, w/w DB) | 11.63% | 13.64% | 37.06% | 42.74% |

Acidification of Liquid Biomass Solution

The liquid biomass solution was decationized using two glass columns in series, 60 liter each, containing cationic resin in acid form (Relite RPS) with a flow rate 4 BV/h (bed volume/hour) to produce an acidic stream. The decationization was performed at 20° C. The LBS stream had a pH of 4.04 and the resulting acidic stream had a pH of 0.97. The acidic stream contained 30% of the initial cations (70% removed). The composition of the acidic stream is contained in Table 5.

The acidic stream was used in all the hydrolysis experiments.

Hydrolysis Reactions

Different hydrolysis experiments were conducted by using the solid samples prepared from S09 and the LCB stream. Acidic stream and solid stream were added into a Parr reactor (model 4560 Mini Bench, top reactor) so to obtain a mixture having a 15% of dry matter by weight.

Table 7 contains the process parameters of the different hydrolysis experiments. The temperature was raised to the reaction temperature in approximately 35 minutes, then it was kept constant for the reaction time, finally temperature was decreased to 25° C. in approximately 40 minutes. The operating parameters (thermal ramp time and temperature, reaction time, pH and reaction temperature) are combined together in the severity factor, which is a single parameter describing the hydrolysis process.

TABLE 7 process parameters of the different hydrolysis experiments.

| Solid | Test 1 S09-ASR | Test 2 S09-W-BRS | Test 3 S09-ASR | Test 4 S09-W-ASR | Test 5 S09-W-BSR |
|---|---|---|---|---|---|
| Washing | — | X | — | X | X |
| Acidic stream | X | X | X | X | X |
| Dry matter (%) | 15% | 15% | 15% | 15% | 15% |
| pH | 1.12 | 0.97 | 1.12 | 0.97 | 0.97 |
| T (° C.) | 197 | 199 | 178 | 178 | 178 |
| time (min) | 20 | 20 | 23 | 23 | 23 |
| SF | 3.06 | 3.21 | 2.53 | 2.67 | 2.67 |

The severity factor is calculated according to the following formula:

$$SF = \log(A/B), \text{ where}$$

$$A = t\exp((T-100)/14.75)$$

$$B = [H^+].$$

t is the time in minutes, T is the temperature in ° C., $[H^+]$ is the proton concentration.

It is noted that the hydrolysis severity factor is different from the severity factor of the thermal treatment, as it is related to a completely different process.

The compositions of the initial mixtures and the composition of reaction products and final pH are reported in the Table of FIG. 18.

Reaction products are analyzed in terms of glucans derived products and xylans derived products. Glucans derived products comprise glucose, and degradation products (HMF, levulinic acid and formic acid) and other glucans degradation products.

Xylans derived products comprise xylose, degradation products (furfural and formic acid) and other xylans degradation products.

Formic acid from glucans is derived from the decomposition of HMF in levulinic acid and formic acid and it is evaluated according to this decomposition reaction. Formic acid from xylans is evaluated as the remnant portion of formic acid present in the reaction products.

Reaction product do not contain glucooligomers and xylooligomers. Degradation products are considered to be hydrolysis products demonstrating the invention, as they are obtained from the monomeric sugars resulted from the hydrolysis of glucans and xylans. Degradation products content may be minimized or eliminated by optimizing the hydrolysis parameters.

Figure 19:
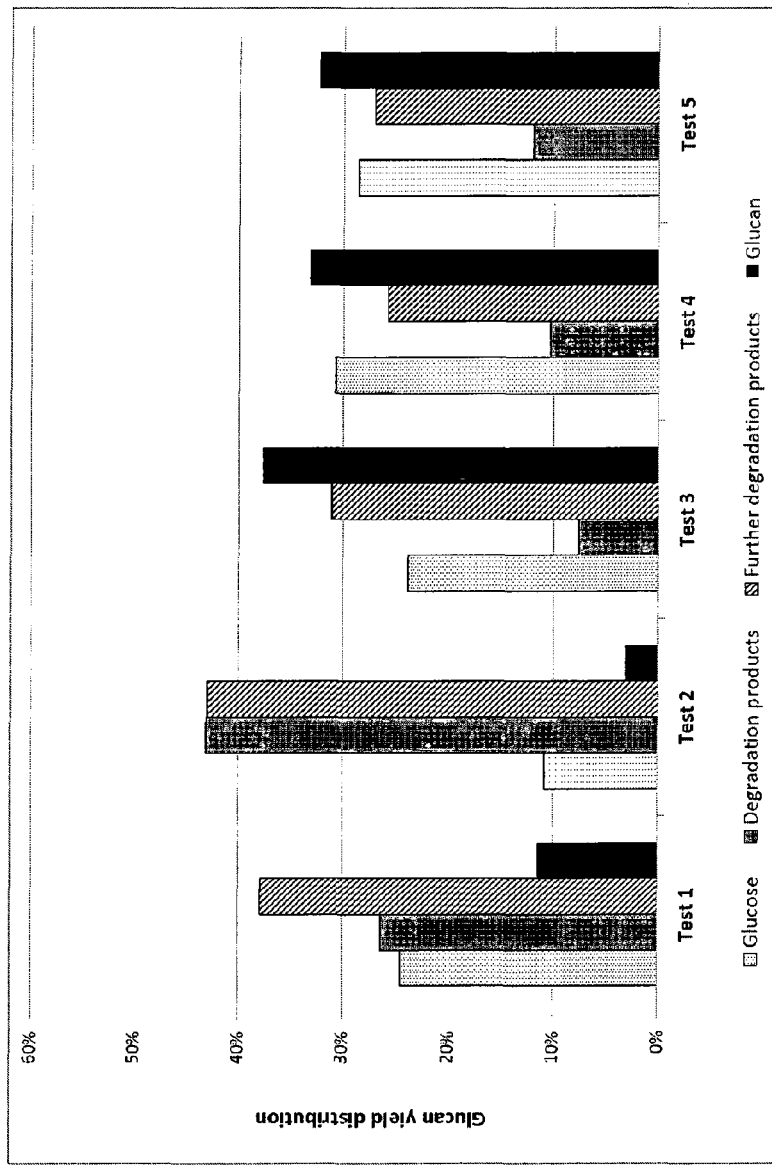
FIG. 19 shows the weight percentage of glucans reaction products with respect to the weight of glucans contained in the starting mixture, according to one embodiment.

FIG. 19 reports the graph of the weight percentage of glucans reaction products with respect to the weight of glucans contained in the starting mixture for all the experiments. The graph contains also the unreacted glucans.

Figure 20:
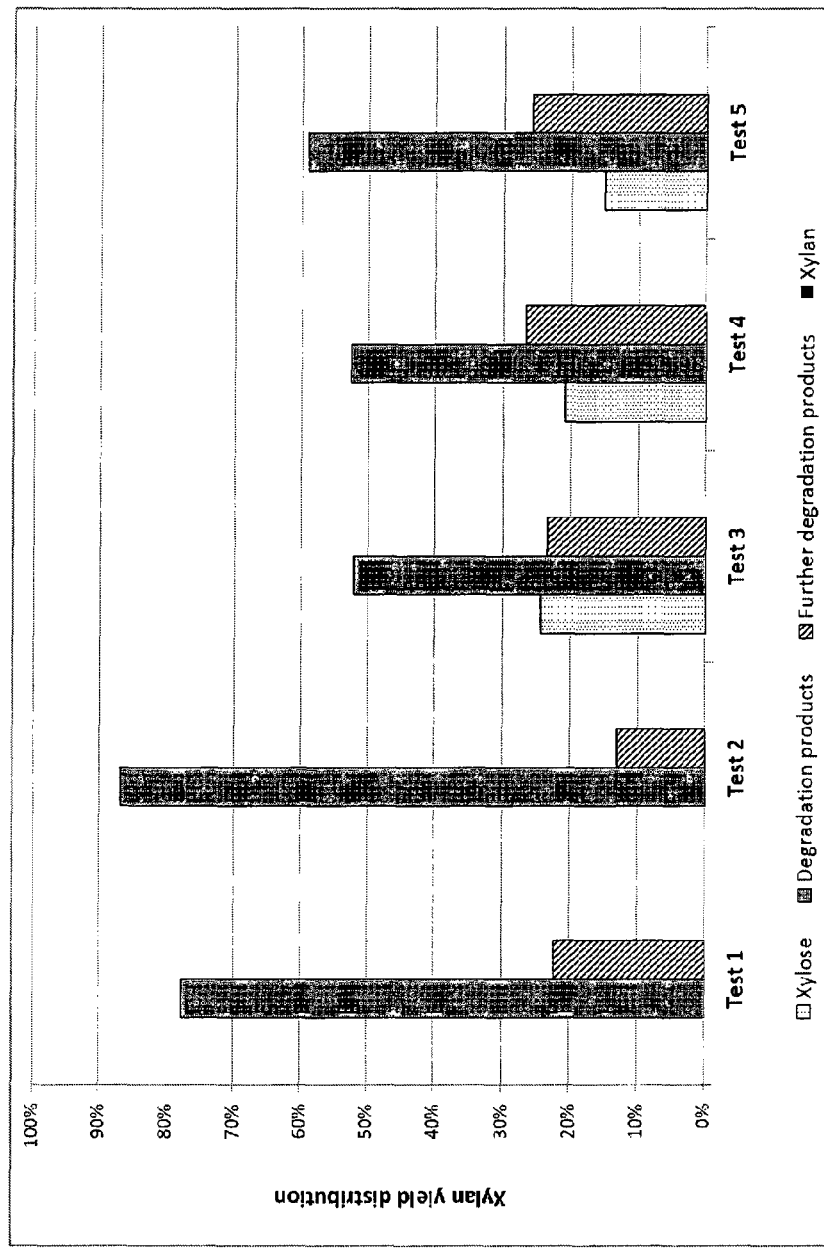
FIG. 20 shows the weight percentage of xylans reaction products with respect to the weight of xylans contained in the starting mixture, according to one embodiment.

FIG. 20 reports the graph of the weight percentage of xylans reaction products with respect to the weight of xylans contained in the starting mixture for all the experiments. The graph contains also the unreacted xylans.

It is noted that the unreacted glucans decrease by increasing severity factors of the reaction and that the disclosed process converts a relevant portion of the glucans in the ligno-cellulosic feedstock. The remnant glucans decrease by increasing the severity factor.

In the case of xylans, all the xylans are converted to xylose, but in the case of test 1 and test 2, having higher severity factors, all the xylose is converted to degradation products.

The invention claimed is:

1. A process for the hydrolysis of C5 and C6 sugars present in a ligno-cellulosic biomass feed stream wherein the process comprises the steps of:
   A. pretreating the ligno-cellulosic biomass feed stream to create a pretreated solid ligno-cellulosic biomass stream comprising water insoluble C6 sugars and a liquid biomass solution comprising water soluble C5 sugars,
   B. creating an acidic stream from the liquid biomass solution by increasing the number of $H^+$ ions in the liquid biomass solution by an amount sufficient so that the pH of the acidic stream is at least 0.5 pH units less than the pH of the liquid biomass solution prior to the addition of the $H^+$ ions, wherein less than 90% of the total amount of H⁺ ions added to the acidic stream are derived from an acid or acids, C. combining at least a portion of the acidic stream comprising water soluble C5 sugars with at least a portion of the water insoluble C6 sugars to create a mixture, and D. hydrolyzing at least one of the C5 and C6 sugars of the mixture by increasing the temperature of the mixture to a hydrolysis temperature greater than 80° C. for a hydrolysis time greater than 0.5 minutes.

2. The process according to claim 1, wherein at least a portion of the H⁺ ions in the acidic stream are derived from decationization of the liquid biomass solution using an ion exchange agent and the at least a portion of the acidic stream mixed with the at least a portion of pretreated solid ligno-cellulosic biomass stream comprising water insoluble C6 sugars is separated from the ion exchange agent before mixing with the at least a pretreated solid ligno-cellulosic biomass stream comprising water insoluble C6 sugars.

3. The process according to claim 1, wherein the percentage of the total amount of H⁺ ions added to the acidic stream derived from an acid or acids is less than 80%.

4. The process according to claim 1, wherein the pH of the acidic stream is less than 2.5.

5. The process according to claim 1, wherein at least a portion of the H⁺ ions is derived from an acid added to either the feed stream or the acidic stream, or both prior to hydrolysis.

6. The process according to claim 1, wherein at least a portion of the H⁺ ions is derived from an acid or acids added to the acidic stream during the hydrolysis step.

7. The process according to claim 1, wherein a salt is added to the process.

8. The process according to claim 7, wherein at least a portion of the salt is added to the feed stream prior to adding the H⁺ ions to create the acidic stream.

9. The process according to claim 1, wherein the hydrolysis temperature range is in the range of 80 to 250° C.

10. The process according to claim 1, wherein the hydrolysis time is within the range of 1 minute to 24 hours.

11. The process according to claim 1, wherein the pretreated solid ligno-cellulosic biomass stream comprising insoluble C6 sugars is thermally treated via steam explosion to create a thermally treated pretreated solid ligno-cellulosic biomass stream comprising insoluble C6 sugars prior to being combined with the at least a portion of the water soluble C5 sugars.

12. The process according to claim 11, wherein the thermally treated pretreated solid lignocellulosic biomass stream comprising insoluble C6 sugars is subjected to a wash process prior to being combined with the at least a portion of the water soluble C5 sugars.

13. The process according to claim 1, wherein the pretreated solid ligno-cellulosic biomass stream comprising insoluble C6 sugars is thermally treated to create a thermally treated ligno-cellulosic biomass stream prior to being combined with the at least a portion of the water soluble C5 sugars.

14. The process according to claim 13, wherein the thermally treated ligno-cellulosic biomass is in physical forms of at least fibres, fines and fiber shives, wherein:

a. the fibres each have a width of 75 µm or less, and a fibre length greater than or equal to 200 µm, b. the fines each have a width of 75 µm or less, and a fine length less than 200 µm, c. the fiber shives each have a shive width greater than 75 µm with a first portion of the fiber shives each having a shive length less than 737 µm and a second portion of the fiber shives each having a shive length greater than or equal to 737 µm;

wherein the process further comprises the step of reducing the fiber shives of the thermally treated ligno-cellulosic biomass, wherein the percent area of fiber shives having a shive length greater than or equal to 737 µm relative to the total area of fiber shives, fibres and fines of the thermally treated ligno-cellulosic biomass after fiber shives reduction is less than the percent area of fiber shives having a shive length greater than or equal to 737 µm relative to the total area of fiber shives, fibres and fines of the thermally treated ligno-cellulosic biomass before fiber shives reduction, wherein the percent area is measured by automated optical analysis.

15. The process according to claim 14, wherein a part of the fiber shives reduction is done by separating at least a portion of the fiber shives having a shive length greater than or equal to 737 µm from the thermally treated ligno-cellulosic biomass.

16. The process of claim 14, wherein a part of the fiber shives reduction is done by converting at least a portion of the fiber shives having a shive length greater than or equal to 737 µm in the thermally treated ligno-cellulosic biomass to fibres or fines.

17. The process of claim 14, wherein at least a part of the fiber shives reduction step is done by applying a work in a form of mechanical forces to the thermally treated lignocellulosic biomass, and all the work done by all the forms of mechanical forces on the thermally treated ligno-cellulosic biomass is less than 500 Wh/Kg per kg of the thermally treated lignocellulosic biomass on a dry basis.

18. The process of claim 17, wherein all the work done by all the forms of mechanical forces on the thermally treated ligno-cellulosic biomass is less than 400 Wh/Kg, per kg of the thermally treated ligno-cellulosic biomass on a dry basis.

19. The process of claim 14, wherein the thermally treated ligno-cellulosic biomass before fiber shives reduction is characterized by having a viscosity of slurry of the thermally treated ligno-cellulosic biomass before fiber shives reduction in water which is greater than the viscosity of a slurry of the thermally treated ligno-cellulosic biomass after fiber shives reduction in water, wherein the viscosities are measured at 25° C., at a shear rate of $10\ s^{-1}$ and at a dry matte content of 7% by weight of each slurry.

20. The process of claim 14, wherein the thermally treated ligno-cellulosic biomass after fiber shives reduction is characterized by having a viscosity of a slurry of the thermally treated ligno-cellulosic biomass after fiber shives reduction in water less than 0.1 Pa s, wherein the viscosity is measured at 25° C., at a shear rate of $10\ s^{-1}$ and at a dry matter content of 7% by weight of the slurry of the thermally treated ligno-cellulosic biomass after fiber shives reduction in the water.

21. The process of claim 14, wherein the percent area of the fiber shives having a shive length greater than or equal to 737 pm relative to the total area of fiber shives, fibres and fines of the thermally treated ligno-cellulosic biomass after fiber shives reduction is less than 5% of the percent area of the fiber shives having a shive length greater than or equal to 737 pm relative to the total area of fiber shives, fibres and fines of the thermally treated ligno-cellulosic biomass before fiber shives reduction.

22. The process of claim 14, wherein the percent area of the fiber shives having a shive length greater than or equal to 737 pm relative to the total area of fiber shives, fibres and fines of the thermally treated ligno-cellulosic biomass after fiber shives reduction is less than 1%.

23. The process of claim 14, wherein the thermally treated lignocellulosic biomass has been steam exploded as part of the thermal treatment.

24. The process of claim 14, wherein the severity factor of the thermal treatment used to create the thermally treated ligno-cellulosic biomass is less than 4.0.

25. The process of claim 14, wherein the thermally treated ligno-cellulosic biomass before fiber shives reduction has a dry matter content of at least 20% by weight of the total content of the thermally treated ligno-cellulosic biomass before fiber shives reduction.

26. The process of claim 25, wherein the dry matter content of the thermally treated ligno-cellulosic biomass before fiber shives reduction is in the range of 25% by weight of the total content of the thermally treated ligno-cellulosic biomass before fiber shives reduction to less than 80% by weight of the total content of the thermally treated ligno-cellulosic biomass after fiber shives reduction.

* * * * *